United States Patent [19]

Ueda et al.

[11] Patent Number: 5,019,500

[45] Date of Patent: May 28, 1991

[54] IGF-I FUSION PROTEINS; PROTECTION OF IGF-I FROM DEGRADATION BY HOST CELL PROTEASES; AND PROCESSES FOR THE PRODUCTION THEREOF

[75] Inventors: Ikuo Ueda, Toyonaka; Mineo Niwa, Mukoo; Yoshimasa Saito, Osaka; Susumu Sato, Osaka; Hiroki Ono, Osaka; Tadashi Kitaguchi, Amagasaki, all of Japan

[73] Assignee: Fujisawa Pharmaceutical Company, Ltd., Osaka, Japan

[21] Appl. No.: 217,885

[22] Filed: Jul. 11, 1988

Related U.S. Application Data

[63] Continuation of Ser. No. 708,636, Mar. 6, 1985, abandoned.

[30] Foreign Application Priority Data

Mar. 19, 1984 [GB]  United Kingdom ............... 8407044
Sep. 25, 1984 [GB]  United Kingdom ............... 8424197

[51] Int. Cl.$^5$ ............... C12N 15/00; C12N 15/17; C12N 15/20; C12N 15/70; C07K 7/40
[52] U.S. Cl. ............... 435/69.1; 435/72.3; 435/252.33; 435/320.1; 536/27; 530/303; 530/350; 530/351; 935/47; 935/60; 935/10; 935/13
[58] Field of Search ............... 435/68, 70, 91, 172.3, 435/320, 317; 530/350, 324, 325, 303, 99, 820; 935/12, 29, 47, 48, 33, 34, 56, 60

[56] References Cited

U.S. PATENT DOCUMENTS 4,571,921  2/1982  Itahu .................... 536/28
4,745,179  5/1988  Ueda et al. ............ 530/350

FOREIGN PATENT DOCUMENTS 0072925  8/1981  European Pat. Off. .
0036726  9/1981  European Pat. Off. .

OTHER PUBLICATIONS

Bau et al., (1913), Abst. presented at ASBC mtg., Jun. 5-9, #434.
Jansen et al., Nature 306, 609-1.
Rinauknecht et al., (1978), J.B.C. 253: 2769-2776.
Nilsson et al., (1985), Nucleic Acids Res. 13(4), 1151-1163.
Gene, (1985), vol. 35, pp. 83-89, "Expression of a Biologically Active Analogue of Somatomedin-C/Insulin-Like ... ", M. Peters et al.
DNA, (1986), vol. 5, pp. 11-20, "A General Method for Retrieving the Components of a Genetically Engineered Fusion Protein", Paula R. Szoka et al.

*Primary Examiner*—Richard A. Schwartz
*Assistant Examiner*—S. L. Nolan
*Attorney, Agent, or Firm*—Oblon, Spivak, McClelland, Maier & Neustadt

[57] ABSTRACT

IGF-I fused with a protective peptide, in which the protective peptide is a protein peptide and is used for the protection of IGF-I from degradation by protease in cells of *E. coli* is disclosed. Also disclosed are genes coding for the fused IGF-I's, plasmids containing the genes, and *E. coli* microorganisms transformed with the plasmids.

11 Claims, No Drawings

IGF-I FUSION PROTEINS; PROTECTION OF IGF-I FROM DEGRADATION BY HOST CELL PROTEASES; AND PROCESSES FOR THE PRODUCTION THEREOF

This is a continuation of application Ser. No. 06/708,636, filed Mar. 6, 1985, now abandoned.

BACKGROUND OF THE INVENTION

1. Field of the Invention

This invention relates to processes for production of human insulin-like growth factor I (hereinafter referred to as IGF-I), to IGF-I fused with a protective peptide (hereinafter referred to as fused IGF-I), to a gene coding for IGF-I, to a gene coding for fused IGF-I, to a plasmid containing IGF-I gene, to a plasmid containing fused IGF-I gene, to a host organism containing plasmid containing IGF-I gene, to a host organism containing plasmid containing fused IGF-I gene, and to processes for the production thereof.

2. Discussion of the Background

Human insulin-like growth factor I is a protein hormone synthesized mainly in human tissues, liver and kidney, stimulated by a certain hormone. It is found in human serum.

IGF-I is known to have insulin-like potency and stimulation potency of sulfate-uptake by cartilage. It may enhance protein and DNA synthesis in a cell.

Therefore, IGF-I is useful as a growth promoter and may be useful in the clinical treatment of diabetes.

IGF-I is excreted in small, amounts in human serum from which it may be isolated in amounts of only a few mgs per several tons of human serum. The producing cell of IGF-I has been isolated in pure form, and it was found that IGF-I biological properties as mentioned above. The amino acid sequence of IGF-I has been reported in the literature.

There exists, however, a need for a method for the more viable commercial production of IGF-I, and such a requirement stimulate the accomplishment of this invention.

SUMMARY OF THE INVENTION

It was perceived by the inventors that the application of recombinant DNA and associated technologies would be the most effective way of producing large quantities of IGF-I.

IGF-I is known to consist of 70 amino acids in the following 70 amino acid sequence:

```
       1                                      10
Gly—Pro—Glu—Thr—Leu—Cys—Gly—Ala—Glu—Leu—
                                              20
Val—Asp—Ala—Leu—Gln—Phe—Val—Cys—Gly—Asp—
                                              30
Arg—Gly—Phe—Tyr—Phe—Asn—Lys—Pro—Thr—Gly—
                                              40
Tyr—Gly—Ser—Ser—Ser—Arg—Arg—Ala—Pro—Gln—
                                              50
Thr—Gly—Ile—Val—Asp—Glu—Cys—Cys—Phe—Arg—
                                              60
Ser—Cys—Asp—Leu—Arg—Arg—Leu—Glu—Met—Tyr—
                                              70
Cys—Ala—Pro—Leu—Lys—Pro—Ala—Lys—Ser—Ala.
```

The inventors of this invention succeeded in producing a large amount of IGF-I by using the following essential steps.

Step 1

A process for the production of a gene coding for IGF-I. This process is optionally followed by a process for the production of fused IGF-I gene, i.e. a gene coding for IGF-I fused with a protective peptide which comprises linking a gene coding for a protective peptide with the IGF-I gene with or without a linker upstream of the IGF-I gene.

Suitable "linkers" may include a gene coding for several amino acids and having a suitable restriction enzyme recognition sites to link a protective peptide upstream of IGF-I gene. The "linker" per se constructs the protective peptide.

The most suitable "linker" are the ones exemplified hereinafter.

Suitable "fused IGF-I, i.e. IGF-I fused with a protective peptide" are the ones as illustrated and exemplified hereinafter in the Examples.

Step 2

A process for the production of an expression vector which comprises inserting a promoter gene and a gene coding for IGF-I or a gene coding for fused IGF-I into a plasmid.

The most suitable "expression vector" may include the plasmid pSdM1-322trp, pLHSdMmtrp, pLHSdMwtrp, pLHSdMctrp and the like.

The most suitable "plasmid" may include pBR322 and the like.

Step 3

A process for the production of a transformant which comprises transforming a host organism with said expression vector.

Suitable "host organism" may include *Escherichia* (hereinafter referred to as *E.) coli* (e. g. *E. coli* HB101, etc.) and the like.

Step 4

A process for the production of IGF-I or fused IGF-I which comprises culturing said transformant in a suitable medium.

Step 5

A process for isolation of IGF-I or fused IGF-I from host organism cells.

Step 6 (optional)

A process for the production of IGF-I which comprises subjecting said fused IGF-I to cleavage reaction condition to cause cleavage of the protective peptide from the fused IGF-I.

BRIEF DESCRIPTION OF THE FIGURES

FIG. 1 parts A–D illustrates the assembly of oligonucleotides from smaller units using successive coupling reactions.

FIG. 2 parts 4–C provides a flow chart of the preparation of the hexadecanucleotide HOApApApCpCpGpApCpCpGpGpCpTpApTpGOH (G1).

FIG. 3 illustrates the construction of the synthetic IGF-I gene.

FIG. 4 illustrates the molecular cloning of the synthetic IGF-I gene.

FIG. 5 illustrates the construction of the synthetic trp promoter I gene.

FIG. 6 illustrates the molecular cloning of the synthetic trp promoter I gene.

FIG. 7 illustrates the construction of the synthetic trp promoter II.

FIG. 8 illustrates the molecular cloning of the synthetic trp promoter II gene.

FIG. 9 illustrates the construction of a protein/peptide LH gene.

FIG. 10 illustrates the molecular cloning of a protein/peptide LH gene.

FIG. 11 illustrates construction of recombinant plasmid pSdMltrp.

FIG. 12 illustrates the construction of recombinant plasmid pSdM1-322trp.

FIG. 13 illustrates the construction of recombinant plasmid pLHtrp.

FIG. 14 illustrates the construction of recombinant plasmid pLHSdMmtrp.

FIG. 15 illustrates the construction of recombinant plasmid pLHSdMwtrp.

FIG. 16 illustrates the construction of recombinant plasmid pLHSdMwtrp.

FIG. 17 illustrates the construction of recombinant plasmid pLHSdMctrp.

FIG. 18 illustrates the construction of recombinant plasmid pLHSdMctrp.

FIG. 19 provides the amino acid sequence analysis of IGF-I.

DETAILED DESCRIPTION OF THE PREFERRED EMBODIMENTS

The "protective peptide" in the term "fused IGF-I, i.e. IGF-I fused with a protective peptide" is a peptide used for protecting IGF-I from degradation by proteases in the cells of a host organism. It is removed by subjecting to cleavage reaction of the fused IGF-I.

The said fused IGF-I is an intermediate for preparing IGF-I by cleavage reaction. The protective peptide thus can be any cleavable protective peptide derived from a natural or a synthetic protein, a natural or synthetic peptide, or a fragment thereof ("protein/peptide" hereinafter).

Suitable "fused IGF-I" may include i) IGF-I fused with a protein/peptide through a methionine residue of the protein/peptide, ii) IGF-I fused with a protein/peptide through a tryptophan residue of the protein/peptide, or iii) IGF-I fused with a protein/peptide through a "-Gly-Pro-Ala-" sequence of the protein/peptide.

Suitable agent used in this cleavage reaction may include cyanogen bromide; (3-bromo-2-o-nitrophenylsulfenyl)skatole (hereinafter referred to as BNPS-skatole) or N-chlorosuccinimide (herein referred to as NCS); collagenase and the like. These can be suitably selected according to the type of the starting fused IGF-I.

In this step, when the protein/peptide is fused with IGF-I through a methionine residue of the protein/peptide, fused IGF-I can be converted to IGF-I by cleavage reaction with cyanogen bromide in high yield.

In addition, when the protein/peptide is fused with IGF-I through a tryptophan residue of the protein/peptide, fused IGF-I can be converted to IGF-I by cleavage reaction with BNPS-skatole or N-chlorosuccinimide.

Further when the protein/peptide is fused with IGF-I through a "-Gly-Pro-Ala-" sequence of the protein/peptide, fused IGF-I can be converted by cleavage reaction to IGF-I with collagenase.

The present cleavage reaction can be conducted under mild conditions in a conventional solvent which does not adversely affect the reaction.

From the above amino acid sequence of IGF-I, a corresponding nucleotide sequence has been invented, subject to a number of specific non-obvious criteria. The IGF-I gene has been cloned by inserting it into a known plasmid, as a cloning vector. The IGF-I gene has been excised from the recombinant plasmid, and then inserted into a plasmid specifically designed to maximize expression of the IGF-I gene under the control of a promoter. A structural gene coding for a protective peptide is optionally inserted into the recombinant plasmid upstream of and adjacent to said IGF-I gene.

Although the present invention is illustrated in detail hereinafter, the present invention is not limited thereto.

[1]Preparation and cloning of a IGF-I gene (1) Preparation of a IGF-I gene

From the above amino acid sequence, because of the diversity of the genetic code, it is possible to predict numerous nucleotide sequences which would code for the IGF-I.

In the determination of an optimum sequence from the large number of possibilities in the present invention, several non-obvious criteria have been observed. Firstly, trinucleotide codons should be used which are acceptable in a host organism to be used. Secondly, it should be desirable to have different restriction enzyme recognition sites at the terminal of the molecule so as to allow insertion into a plasmid in a desired orientation. Moreover, it should be decided to select sites which will allow to use well known cloning vectors. Thirdly, the synthesis should not be unnecessarily complicated, and illegitimate cross-hybridization should be minimized in order to facilitate gene assembly, so that stable off-diagonal interactions might be avoided as far as possible.

One of the preferred sequence selected for the coding for portion of the IGF-I gene is as follows:

```
              1
           Gly   Pro   Glu   Thr   Leu   Cys
Coding:    5'-GGT—CCT—GAA—ACT—CTG—TGC—
Noncoding: 3'-CCA—GGA—CTT—TGA—GAC—ACG—

10
Gly   Ala   Glu   Leu   Val   Asp   Ala   Leu
GGC—GCT—GAA—CTG—GTT—GAC—GCT—CTG—
CCG—CGA—CTT—GAC—CAA—CTG—CGA—GAC—

20
Gln   Phe   Val   Cys   Gly   Asp   Arg   Gly
CAA—TTT—GTA—TGT—GGT—GAT—CGT—GGT—
GTT—AAA—CAT—ACA—CCA—CTA—GCA—CCA—

30
Phe   Tyr   Phe   Asn   Lys   Pro   Thr   Gly
TTC—TAC—TTC—AAC—AAA—CCG—ACC—GGC—
AAG—ATG—AAG—TTG—TTT—GGC—TGG—CCG—
```

-continued

```
    Tyr Gly Ser Ser Ser Arg Arg Ala
    TAT-GGC-TCC-AGC-TCT-CGT-CGC-GCA-
    ATA-CCG-AGG-TCG-AGA-GCA-GCG-CGT-

40
    Pro Gln Thr Gly Ile Val Asp Glu
    CCG-CAG-ACT-GGT-ATC-GTA-GAC-GAA-
    GGC-GTC-TGA-CCA-TAG-CAT-CTG-CTT-

50
    Cys Cys Phe Arg Ser Cys Asp Leu
    TGC-TGT-TTT-CGT-TCT-TGC-GAT-CTC-
    ACG-ACA-AAA-GCA-AGA-ACG-CTA-GAG-

60
    Arg Arg Leu Glu Met Tyr Cys Ala
    CGC-CGT-CTG-GAA-ATG-TAC-TGT-GCT-
    GCG-GCA-GAC-CTT-TAC-ATG-ACA-CGA-

70
    Pro Leu Lys Pro Ala Lys Ser Ala
    CCA-CTG-AAG-CCA-GCA-AAA-TCC-GCG-3'
    GGT-GAC-TTC-GGT-CGT-TTT-AGG-CGC-5'
```

In the sequences in this specification A, G, C and T represent the following formulae

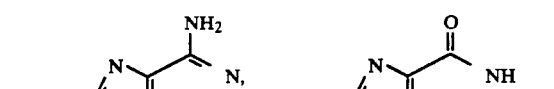
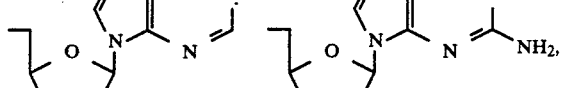
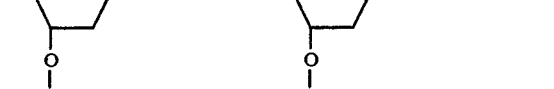
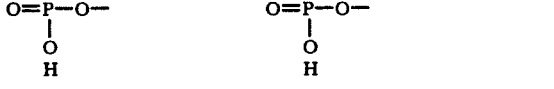

respectively, and 5'-terminal A, G, C and T represent the following formulae:

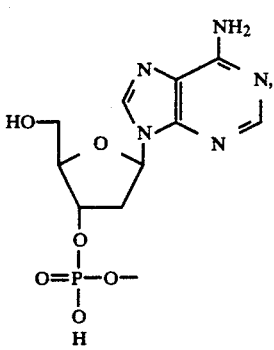
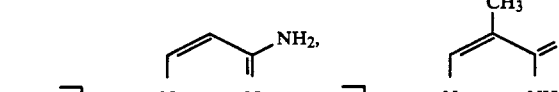
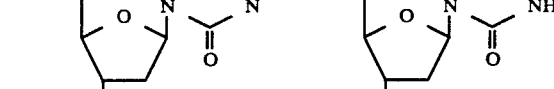

respectively, and 3'-terminal A, G, C and T represent the following formulae:

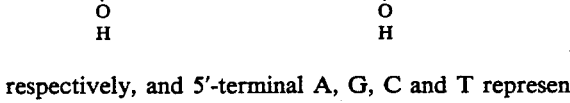
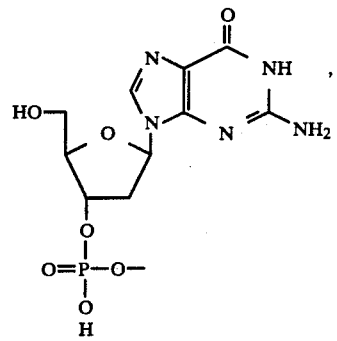

respectively.

Considering the above-mentioned criteria, particularly in consideration of the second criteria mentioned above, the following slightly longer sequence can be selected.

Accordingly, in a suitable embodiment of this invention, EcoRI and BamHI sites can be selected and introduced at the 5' and 3' ends, respectively.

Further, a methionine codon (ATG) was inserted upstream of and adjacent to the N-terminal amino acid codon of IGF-I, and two stop codons (TGA and TAG) were inserted downstream of and adjacent to the C-terminal codon.

```
                    (AvaII)
           EcoRI   Met  Gly  Pro  Glu  Thr
Coding:    5'-AATTC—ATG—GGT—CCT—GAA—ACT—
Noncoding:     3'-G—TAC—CCA—GGA—CTT—TGA—

10
Leu  Cys  Gly  Ala  Glu  Leu  Val  Asp
CTG—TGC—GGC—GCT—GAA—CTG—GTT—GAC—
GAC—ACG—CCG—CGA—CTT—GAC—CAA—CTG—

20
Ala  Leu  Gln  Phe  Val  Cys  Gly  Asp
GCT—CTG—CAA—TTT—GTA—TGT—GGT—GAT—
CGA—GAC—GTT—AAA—CAT—ACA—CCA—CTA—

Arg  Gly  Phe  Tyr  Phe  Asn  Lys  Pro
CGT—GGT—TTC—TAC—TTC—AAC—AAA—CCG—
GCA—CCA—AAG—ATG—AAG—TTG—TTT—GGC—

30
Thr  Gly  Tyr  Gly  Ser  Ser  Ser  Arg
ACC—GGC—TAT—GGC—TCC—AGC—TCT—CGT—
TGG—CCG—ATA—CCG—AGG—TCG—AGA—GCA—

40
Arg  Ala  Pro  Gln  Thr  Gly  Ile  Val
CGC—GCA—CCG—CAG—ACT—GGT—ATC—GTA—
GCG—CGT—GGC—GTC—TGA—CCA—TAG—CAT—

50
Asp  Glu  Cys  Cys  Phe  Arg  Ser  Cys
GAC—GAA—TGC—TGT—TTT—CGT—TCT—TGC—
CTG—CTT—ACG—ACA—AAA—GCA—AGA—ACG—

60
Asp  Leu  Arg  Arg  Leu  Glu  Met  Tyr
GAT—CTC—CGC—CGT—CTG—GAA—ATG—TAC—
CTA—GAG—GCG—GCA—GAC—CTT—TAC—ATG—

Cys  Ala  Pro  Leu  Lys  Pro  Ala  Lys
TGT—GCT—CCA—CTG—AAG—CCA—GCA—AAA—
ACA—CGA—GGT—GAC—TTC—GGT—CGT—TTT—

70
Ser  Ala  stop  stop  BamHI
TCC—GCG—TGA—TAG-3'
AGG—CGC—ACT—ATC—CTAG-5'
```

The present invention also relates to a process for the production of such a gene. This process comprises hybridization and ligation of a number of the corresponding oligonucleotide blocks.

(i) Synthesis of oligonucleotides

A molecule having the above expanded sequence was synthesized by making 30 synthetic oligonucleotides, which will hybridize and were ligated in pre-determined stages to give the double-stranded nucleotide sequence mentioned above.

In the synthesis of oligonucleotides set out in this specification, the following abbreviations are used.

Ap, Gp, Cp and Tp represent the following formulae:

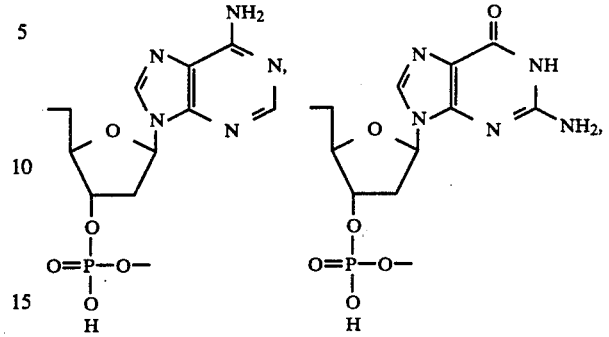

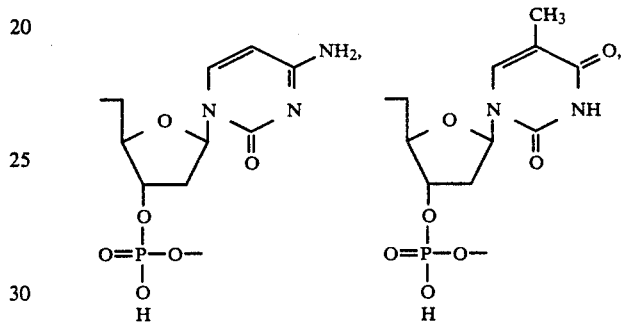

respectively, and

3'-terminal A, G, C and T represent the following formulae:

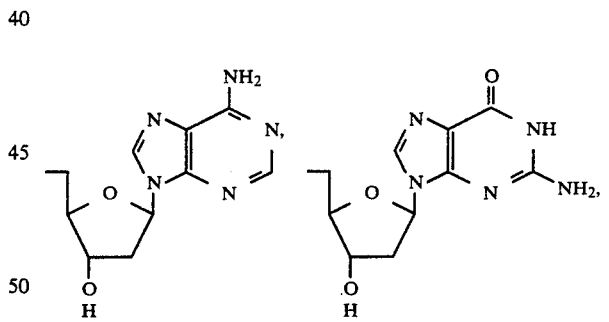

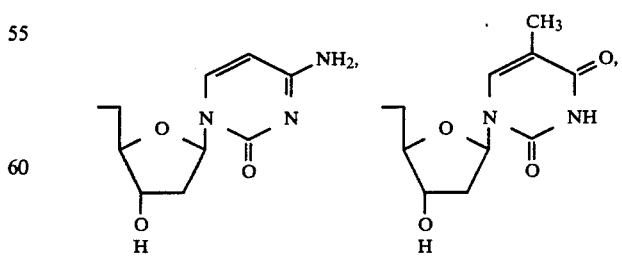

respectively, and $A^{Bz}po$, $G^{iB}po$, $C^{Bz}po$, Tpo and $^{Ac}Upo$ represent the following formulae:

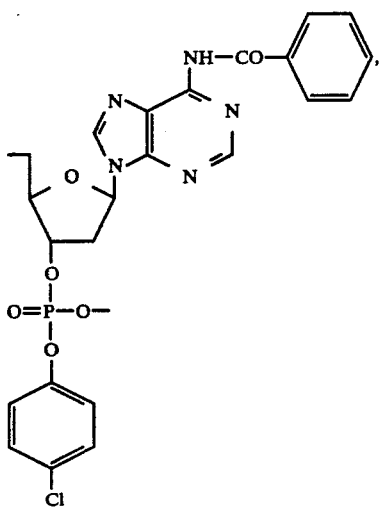

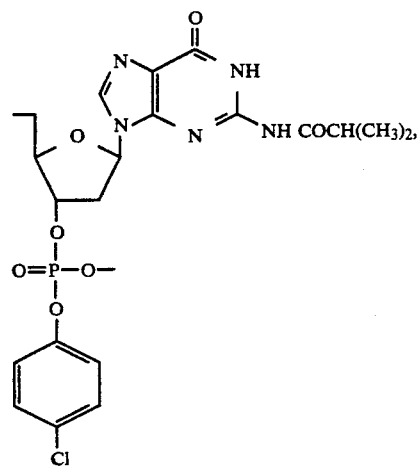

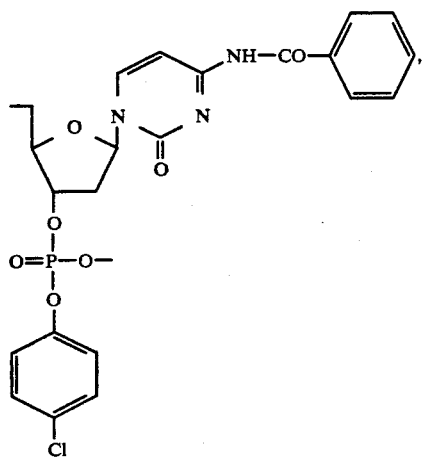

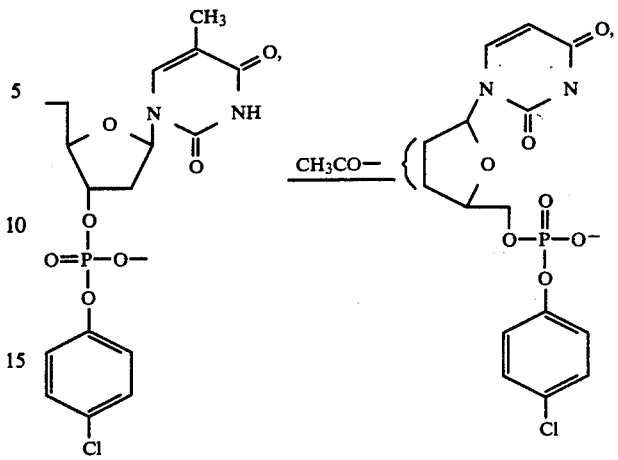

-continued respectively, and
DMTr is dimethoxytrityl,
B is a base selected from adeninyl, guaninyl, cytosinyl and thyminyl (for convenience, protecting group are not shown),
U is uracyl,
Ac is acetyl,
m is an integer of 1 or 2, and
n is an integer of 1 to 12.

The oligonucleotides are as follows:
(1) HOApApTpTpCpApTpGpGpGpTOH (A1)
(2) HOTpTpTpCpApGpGpApCpCpCpApTpGOH (A2)
(3) HOCpCpTpGpApApApCpTpCpTpGpTpGOH (B1)
(4) HOCpApGpCpGpCpCpGpCpApCpApGpAp-GOH (B2)
(5) HOCpGpGpCpGpCpTpGpApApCpTpGpG-pTOH (C1)
(6) HOApGpApGpCpGpTpCpApApCpCpApGpT-pTOH (C2)
(7) HOTpGpApCpGpCpTpCpTpGpCpApApTpT-pTOH (D1)
(8) HOCpCpApCpApTpApCpApApApTpTpGpCOH (D2)
(9) HOGpTpApTpGpTpGpGpTpGpApTpCpG-pTOH (E1)
(10) HOTpApGpApApApCpCpApCpGpApTp-CpAOH (E2)
(11) HOGpGpTpTpTpCpTpApCpTpTpCpApAp-COH (F1)
(12) HOGpGpTpCpGpGpTpTpTpGpTpTpGpApAp-GOH (F2)
(13) HOApApApCpCpGpApCpCpGpGpCpTpApT-pGOH (G1)
(14) HOGpCpTpGpGpApGpCpCpApTpApGpC-pCOH (G2)
(15) HOGpCpTpCpCpApGpCpTpCpTpCpGpT-pCOH (H1)
(17) HOGpCpGpCpApCpGpGpCpApGpApCpT-pGOH (I1)
(18) HOCpTpApCpGpApTpApCpCpApGpTpCpT-pGOH (I2)
(19) HOGpTpApTpCpGpTpApGpApCpGpApApT-pGOH (J1)
(20) HOGpApApApApCpApGpCpApTpTpCpG-pTOH (J2)

(21) HOCpTpGpTpTpTpTpCpGpTpTpCpTpTpGOH (K1)
(22) HOGpGpApGpApTpCpGpCpApApGpApApCOH (K2)
(23) HOCpGpApTpCpTpCpCpGpCpCpGpTpCpTOH (L1)
(24) HOTpApCpApTpTpTpCpCpApGpApCpGpGpCOE (L2)
(25) HOGpGpApApApTpGpTpApCpTpGpTpGpCpTOH (M1)
(26) HOTpTpCpApGpTpGpGpApGpCpApCpApGOH (M2)
(27) HOCpCpApCpTpGpApApGpCpCpApGpCpAOH (N1)
(28) HOGpCpGpGpApTpTpTpTpGpCpTpGpGpCOH (N2)
(29) HOApApApTpCpCpGpCpGpTpGpApTpApGOH (O1)
(30) HOGpApTpCpCpTpApTpCpApCOH (O2)

The methods of building up oligonucleotides from smaller units by successive coupling reactions are set out below.

The successive coupling reaction is shown in Fig 1.

Mono(or di, or tri)mer (I) can be prepared by the Hirose's method [T. Hirose, PROTEIN, NUCLEIC ACID AND ENZYME ISSN, 25, 225(1980), published in Japan], and coupling can be carried out on cellulose by a phosphotriester method [R. Crea et al, Nucleic Acid Research 8, 2331(1980) and M. L. Duckworth et al, Nucleic Acid Research, 9, 1691(1981)].

Particularly, the synthetic methods will now be illustrated with reference to the synthesis of the hexadecanucleotide HOApApApCpCpGpApCpCpGpGpCpTpApTpGOH (G1) described in Example 1. The flow chart of the synthesis of the hexadecanucleotide G1 is shown in FIG. 2.

(ii) Hybridization and ligation of the chemically synthesized oligonucleotide:

The oligonucleotides are hybridized and ligated in a series of steps, minimizing the possibilities for undesirable interactions as shown in FIG. 3. In FIG. 3, an oligonucleotide is illustrated as ● (● means 5'-phosphorylated end), and blocked oligonucleotides are illustrated, for example, as ● (● means a ligated position). Ligation is conducted in the presence of T4 DNA ligase.

Oligonucleotides A1, B1 and A2; C1, B2 and C2; D1, E1 and D2; F1, E2, and F2; G1, H1, and G2; I1, H2 and I2; J1, K1 and J2; L1, K2 and L2; M1, N1 and M2 and O1, N2 and O2 were hybridized and ligated to give Blocks 1 to 10, respectively. In this case Blocks 1 and 10 which were obtained from oligonucleotides A1, B1 and A2, and O', N2 and O2, respectively, hybridized and ligated each other to form dimers. Blocks 2 and 3; 4 and 5, 6 and 7, 8 and 9 were hybridized and ligated to give Blocks 11, 12, 13 and 14, respectively. Blocks 11 and 12; 13 and 14 were hybridized and ligated to form Blocks 15 and 16, respectively. Blocks 1, 15, 16 and 10 were hybridized and ligated. The thus obtained ligated mixture was cleaved by EcoRI and BamHI to give a target polynucleotide IGF-I gene.

(2) Molecular cloning of the IGF-I gene:

In order to clone the IGF-I gene, it is inserted into an appropriate plasmida, cloning vector, having suitable enzyme recognition sites in which the IGF-I gene can be inserted.

In a suitable embodiment of this invention the IGF-I gene synthesized for the expression in *E. coli* was inserted into a plasmid originated in *E. coli* (e.g. pBR322, etc.) and cloning was conduced.

For example, in using plasmid pBR322 (which is commercially available) which has EcoRI and BamHI sites, as shown in FIG. 4, the plasmid was cleaved by EcoRI and BamHI. In this case the plasmid codes for ampicillin resistance (indicated by Amp) on the longer fragment when cleaved by EcoRI and BamHI, and the coding for tetracycline resistance code (indicated by Tet) vanishes as a consequence of cleavage at the BamHI site. The longer fragment of EcoRI, BamHI-cleaved plasmid pBR322, was purified by electroelution, hybridized and ligated with a large excess of the IGF-I gene using T4 DNA ligase. The obtained mixture was transformed into *E. coli* HB101 (ATCC 33694). The plasmid was isolated from one of the several ampicillin resistant and tetracycline sensitive transformants obtained and confirmed to contain the IGF-I gene by digestion with restriction enzyme and electrophoresis. This process is shown in FIG. 4. Thus obtained plasmid is named plasmid pSdM1.

(3) Sequence of the IGF-I gene in plasmid pSdM1

The Maxam-Gilbert method can be used.

For sequencing the IGF-I gene, plasmid pSdM1 was digested with EcoRI and then treated with AMV reverse transcriptase in the presence of $\alpha$-$^{32}$P-ATP. The linear plasmid labeled with $^{32}$P was digested with BamHI to give two fragments (224 bp, 4.0 kbp). The smaller fragment (224 bp) was analyzed by the Maxam-Gilbert method [A. Maxam and W. Gilbert, Proc. Natl. Acad. Sci. USA 74, 560 (1977)]. On the other hand, plasmid pSdM1 was digested with BamHI firstly, and then labeled with $^{32}$P as described above. The linear plasmid was digested with EcoRI to give two fragments (224 bp, 4.0 kbp). The smaller fragment (224 bp) was analyzed by Maxam-Gilbert method. The results of sequencing from both side of the IGF-I gene agreed with the designed IGF-I gene.

[2] Preparation and cloning of a promoter gene

To obtain fused IGF-I from a host organism, a promoter gene was designed.

A promoter gene is inserted into a plasmid in a manner appropriate is that the promoter gene is located upstream of and adjacent to a gene coding for IGF-I or fused IGF-I.

In a suitable embodiment of this invention a synthetic trp promoter I gene or a synthetic trp promoter II gene was prepared.

(1) Preparation and cloning of a synthetic trp promoter I gene:

A molecule having 107 was synthesized by making 14 synthetic oligonucleotide blocks, which were assembled by single-strand overlaps to give the complete double stranded nucleotide sequence.

```
      EcoRI*
5'-AATTTGCCGACATCATAACGGTTCTGGCAAATAT
3'-    ACGGCTGTAGTATTGCCAAGACCGTTTATA

TCTGAAATGAGCTGTTGACAATTAATCATCGAACT
AGACTTTACTCGACAACTGTTAATTAGTAGCTTGA

AGTTAACTAGTACGCAAGTTCACGTAAAAGGGTA
TCAATTGATCATGCGTTCAAGTGCATTTTTCCCAT
```

EcoRI
TCG-3'
AGCTTAA-5'

(i) Synthesis of oligonucleotides

The oligonucleotide blocks are as follows:
(1) HOApApTpTpGpCpCpGpApCpAOH (A)
(2) HOCpGpTpTpApTpGpApTpGpTpCpGpGp-CpAOH (B)
(3) HOTpCpApTpApApCpGpGpTpTpCpTpGpG-pCOH (C)
(4) HOGpApApTpApTpTpTpGpCpCpApGpApAp-COH (D)
(5) HOApApApTpApTpTpCpTpGpApApApTpG-pAOH (E)
(6) HOTpCpApApCpApGpCpTpCpApTpTpTp-CpAOH (F)
(7) HOGpCpTpGpTpTpGpApCpApApTpTpApAp-TOH (G)
(8) HOGpTpTpCpGpApTpGpApTpTpApApTpT-pGOH (H)
(9) HOCpApTpCpGpApApCpTpApGpTpTpApAp-COH (I)
(10) HOGpCpGpTpApCpTpApGpTpTpApApCp-TpAOH (J)
(11) HOTpApGpTpApCpGpCpApApGpTpTpCpAp-COH (K)
(12) HOCpTpTpTpTpApCpGpTpGpApApCpT-pTOH (L)
(13) HOGpTpApApApApApGpGpTpApTpC-pGOH (M)
(14) HOApApTpTpCpGpApTpApCpCOH (N)

The synthetic method will now be illustrated with reference to the synthesis of the hexadecanucleotide HOApApApCpCpGpApCpCpGpGpCpTpApT-pGOH (G1) mentioned above.

(ii) Ligation of chemically synthesized oligonucleotide

The oligonucleotides were hybridized and ligated using a protocol similar manner to that used for the IGF-I gene as shown in FIG. 5.

(iii) Molecular cloning of the synthetic trp promoter I gene

In order to clone the synthetic trp promoter I gene, the synthetic trp promoter gene is inserted into an appropriate plasmid having suitable enzyme recognition sites in which the synthetic trp promoter I gene can be inserted. In a suitable embodiment of this invention, cloning was conducted by using a plasmid pBR325 (commercially available) as shown in FIG. 6. The plasmid pBR325 was cleaved with EcoRI, and the synthetic trp promoter I gene was inserted thereto. The thus obtained plasmid is named plasmid pST-1. The plasmid pST-1 was transformed into E. coli HB101.

(2) Preparation of synthetic trp promoter II gene

To insert the synthetic trp promoter I described above in a correct direction into a plasmid, following a synthetic promoter, synthetic trp promoter II, having a certain length of base pair chain following the EcoRI site of synthetic trp promoter I and the BamHI site at 3'-end, was prepared.

A molecule having 163 bp was synthesized by making 22 synthetic oligonucleotide blocks, which were assembled by single-strand overlaps to give the complete double-stranded nucleotide sequence.

EcoRI*
5'-AATTTGCCGACATCATAACGGTTCTGGCAAATAT
3'-     ACGGCTGTAGTATTGCCAAGACCGTTTATA

TCTGAAATGAGCTGTTGACAATTAATCATCGAACT
AGACTTTACTCGACAACTGTTAATTAGTAGCTTGA

AGTTAACTAGTACGCAAGTTCACGTAAAAAGGGTA
TCAATTGATCATGCGTTCAAGTGCATTTTTCCCAT

EcoRI
TCGAATTCATGGCTGGTTGTAAGAACTTCTTTTGG
AGCTTAAGTACCGACCAACATTCTTGAAGAAACC

BamHI
AAGACTTTCACTTCGTGTTGATAG-3'
TTCTGAAAGTGAAGCACAACTATCCTAG-5'

(i) Synthesis of oligonucleotides

Eight oligonucleotide was further synthesized.
(1) HOApApTpTpCpApTpGpGpCpTOH (SA)
(2) HOGpGpTpTpGpTpApApGpApApCpTpTpC-pTOH (SB)
(3) HOTpTpTpGpGpApApGpApCpTpTpTOH (SC)
(4) HOCpApCpTpTpCpGpTpGpTpTpGpApTpAp-GOH (SD)
(5) HOTpTpApCpApApCpCpApGpCpCpApTpGOH (SE)
(6) HOCpCpApApApApGpApApGpTpTpCOH (SF)
(7) HOCpGpApApGpTpGpApApApGpTpCpT-pTOH (SG)
(8) HOGpApTpCpCpTpApTpCpApApCpApAOH (SH)

The synthetic method will now be illustrated with reference to the synthesis of the hexadecanucleotide HOApApApCpCpGpApCpCpGpGpCpTpApT-pGOH (G1) mentioned above.

(ii) Hybridization and ligation of chemically synthesized oligonucleotides

The oligonucleotide A to N and SA to SH were hybridized, and ligated using a protocol similar to that used for the IGF-I gene as shown in FIG. 7.

(3) Molecular cloning of synthetic trp promoter II gene

The synthetic trp promoter II gene was inserted into a plasmid. In a suitable embodiment of this invention, the synthetic trp promoter II was inserted into a plasmid pBR322 by cleaving the plasmid with EcoRI and BamHI as shown in FIG. 8. Thus obtained plasmid is named as plasmid pTrpEB7.

1 [3] Preparation and cloning of protein/peptide LH gene

As a suitable example of a protective peptide which can be fused with IGF-I, protein/peptide LH was prepared ("LH" is used in this text to designate a protein/peptide derived from the left hand of γ-interferon).

(1) Preparation of protein/peptide LH gene

A molecule having 233 bp was synthesized by making 32 synthetic oligonucleotide blocks, which were assembled by single-strand overlaps to give the complete double stranded nucleotide sequence.

```
                    1
          EcoRI   Met  Cys  Tyr  Cys  Gln
Coding:    5'-AATTC—ATG—TGT—TAC—TGC—CAG—
Noncoding:     3'-G—TAC—ACA—ATG—ACG—GTC—

10
Asp  Pro  Tyr  Val  Lys  Glu  Ala  Glu
GAC—CCA—TAT—GTA—AAA—GAA—GCA—GAA—
CTG—GGT—ATA—CAT—TTT—CTT—CGT—CTT—

20
Asn  Leu  Lys  Lys  Tyr  Phe  Asn  Ala
AAC—CTT—AAG—AAA—TAC—TTT—AAT—GCA—
TTG—GAA—TTC—TTT—ATG—AAA—TTA—CGT—

Gly  His  Ser  Asp  Val  Ala  Asp  Asn
GGT—CAT—TCA—GAT—GTA—GCG—GAT—AAT—
CCA—GTA—AGT—CTA—CAT—CGC—CTA—TTA—

30
Gly  Thr  Leu  Phe  Leu  Gly  Ile  Leu
GGA—ACT—CTT—TTC—TTA—GGC—ATT—TTG—
CCT—TGA—GAA—AAG—AAT—CCG—TAA—AAC—

40
Lys  Asn  Trp  Lys  Glu  Glu  Ser  Asp
AAG—AAT—TGG—AAA—GAG—GAG—AGT—GAC—
TTC—TTA—ACC—TTT—CTC—CTC—TCA—CTG—

50
Arg  Lys  Ile  Met  Gln  Ser  Gln  Ile
AGA—AAA—ATA—ATG—CAG—AGC—CAA—ATT—
TCT—TTT—TAT—TAC—GTC—TCG—GTT—TAA—

HindIII  60
Val  Ser  Phe  Tyr  Phe  Lys  Leu  Phe
GTC—TCC—TTT—TAC—TTC—AAG—CTT—TTC—
CAG—AGG—AAA—ATG—AAG—TTC—GAA—AAG—

Lys  Asn  Phe  Lys  Asp  Asp  Gln  Ser
AAA—AAC—TTT—AAG—GAT—GAC—CAG—AGC—
TTT—TTG—AAA—TTC—CTA—CTG—GTC—TCG—

70
Ile  Gln  Lys  Ser  Val  Stop
ATC—CAA—AAG—AGT—GTG—TAA—
TAG—GTT—TTC—TCA—CAC—ATT—

Stop     BamHI
TGA—TAG
ACT—ATCCTAG
```

(i) Oligonucleotides synthesis

The oligonucleotide blocks are as follows:
(1) HOApApTpTpCpApTpGpTpGpTpTOH (a1)
(2) HOApCpTpGpCpCpApGpGpApCpCpCpAp-TOH (a2)
(3) HOApTpGpTpApApApApGpApApGpCpAp-GOH (a3)
(4) HOTpGpGpCpApGpTpApCpApCpApT-pGOH (a4)
(5) HOTpTpTpApCpApTpApTpGpGpGpTpCpCOH (a5)
(6) HOApApGpGpTpTpTpTpCpTpGpCpTpTpC-pTOH (a6)
(7) HOApApApApCpCpTpTpApApGpApApApT-pAOH (b1)
(8) HOCpTpTpTpApApTpGpCpApGpGpTpCpAOH (b2)
(9) HOTpTpCpApGpApTpGpTpApGpCpGpG-pAOH (b3)
(10) HOApTpTpApApApGpTpApTpTpTpCpT-pTOH (b4)
(11) HOApTpCpTpGpApApTpGpApCpCpTpG-pCOH (b5)
(12) HOTpTpCpCpApTpTpApTpCpCpGpCpTpAp-COH (b6)
(13) HOTpApApTpGpGpApApCpTpCpTpTpTpT-pCOH (c1)
(14) HOTpTpApGpGpCpApTpTpTpTpGpApAp-GOH (c2)
(15) HOApApTpTpGpGpApApApApGpApGpGpAp-GOH (c3)
(16) HOTpGpCpCpTpApApGpApApApApGpAp-GOH (c4)
(17) HOTpCpCpApApTpTpCpTpTp-CpApApApAOH (c5)
(18) HOCpTpGpTpCpApCpTpCpTpCpTpCpT-pTOH (c6)
(19) HOApGpTpGpApCpApGpApApApApApT-pAOH (d1)
(20) HOApTpGpCpApGpApGpCpCpApApApT-pTOH (d2)
(21) HOGpTpCpTpCpCpTpTpTpTpApCpTpTOH (d3)
(22) HOCpTpCpTpGpCpApTpTpApTpTpTpT-pTOH (d4)
(23) HOApGpGpApGpApCpApApTpTpTpGpGOH (d5)
(24) HOApApApGpCpTpTpGpApApGp-TpApApAOH (d6)
(25) HOCpApApGpCpTpTpTpTp-CpApApApApAOH (e1)
(26) HOCpTpTpTpApApGpGpApTpGpApCp-CpAOH (e2)
(27) HOGpApGpCpApTpCpCpApApApApGpAp-GOH (e3)
(28) HOCpCpTpTpApApApApGpTpTpTpTpG-pAOH (e4)
(29) HOGpGpApTpGpCpTpCpTpGpGpTpCpAp-TOH (e5)
(30) HOTpGpTpGpTpApApApTpGpApTpApGOH (11)
(31) HOTpApCpApCpApCpTpCpTpTpTpTOH (12)
(32) HOGpApTpCpCpTpApTpCpApTOH (13)

(ii) Hybridization and ligation of chemically synthesized oligonucleotides

The oligonucleotides a1 to 13 were hybridized and ligated protocol a similar to that used for the IGF-I gene as shown in FIG. 9.

(2) Molecular cloning of protein/peptide LH gene

The protein/peptide LH gene was inserted into a plasmid. In a suitable embodiment of this invention, protein/peptide LH gene was inserted into a plasmid pBR322 by cleaving the plasmide, with EcoRI and BamHI as shown in FIG. 10. The thus obtained plasmid is named plasmid pLH107.

[4] Construction of an expression vector of IGF-I

The IGF-I gene is inserted into a plasmid containing a promoter gene, and the IGF-I gene is transformed into a host organism.

In a suitable embodiment of this invention, the following recombinant plasmids were established to express the IGF-I gene in E. coli.

(1) Construction of recombinant plasmid pSdMltrp

Trp promoter plasmid pST-1 prepared above was digested with EcoRI and the IGF-I gene was inserted to the resulting large fragment. The thus obtained recombinant plasmid was named plasmid pSdMltrp which was transformed into *E. coli*, for example *E. coli* HB101. This process is shown in FIG. 11.

(2) Construction of recombinant plasmid pSdMl-322trp

Trp promoter plasmid pTrpEB7 was digested with EcoRI and BamHI. The resulting large fragment (4.1 kbp) was separated by agarose gel electrophoresis. On the other hand, the IGF-I gene was isolated from plasmid pSdMl, and ligated with the above promoter vector (4.1 kbp). The mixture was transformed into *E. coli* HB101. The plasmid was isolated from one of the ampicillin resistant and tetracycline sensitive transformants obtained, and confirmed to contain the IGF-I gene by digestion with restriction enzyme and electrophoresis. The thus obtained plasmid was named plasmid pSdMl-322trp and the *E. coli* containing the plasmid was named *E. coli* F-3. This process is shown in FIG. 12.

[5] Sequencing of the IGF-I gene and the promoter gene The Maxam Gilbert method can be used.

(1) Sequence of the IGF-I gene and the synthetic trp promoter I gene in plasmid pSdMltrp The sequence of IGF-I and the synthetic trp promoter I in plasmid pSdMl-322trp was determined using a protocol similar to that used for plasmid pSdMl-322trp described below.

(2) Sequence of IGF-I gene and synthetic trp promoter I gene in plasmid pSdMl-322trp For sequencing IGF-I and the synthetic trp promoter I gene, plasmid pSdMl-322trp was digested with EcoRI and treated with BAP (bacteria alkaline phosphatase), and then treated with T4 polynucleotide kinase in the presence of $\gamma$-$^{32}$P-ATP. The labeled DNA was digested with HinfI to give two fragments (110 bp and 480 bp). These fragments were analyzed by the Maxam-Gilbert method. (A. Maxam and W. Gilbert, Proc. Natl. Acad. Sci. USA 74, 560 (1977)). The resulting sequence coincided with the designed sequence of the IGF-I gene and the synthetic promoter I gene.

[6] Construction of an expression vector for fused IGF-I

A gene coding for fused IGF-I which comprises linking a gene coding for a protective peptide with IGF-I gene with or without a linker upstream of the IGF-I gene was prepared.

In this process, the following three types of protein/peptides are fused with IGF-I.

Type I: a protein/peptide having a methionine residue as the last amino acid

Type II: a protein/peptide having a tryptophan residue as the last amino acid

Type III: a protein,/peptide having the sequence -Gly-Pro-Ala- as the last amino acids The thus obtained three types of fused IGF-I are as follows.

Type I: IGF-I fused with the protein,/peptide through a methionine residue of the protein/peptide Type II: IGF-I fused with the protein/peptide through a tryptophan residue of the protein/peptide Type III: IGF-I fused with the protein/peptide through the sequence "-Gly-Pro-Ala-" of the protein/peptide The present invention also relates to expression vectors of a gene coding these three types of fused IGF-I.

The present invention also relates to expression vectors of a gene coding these three types of fused IGF-I.

In a suitable embodiment of this invention, the following types of expression vector of a gene coding for IGF-I fused with protein/peptide LH were prepared.

The present invention also relates to a process for the invention of such a gene which is constructed by linking a gene coding for a protective peptide with the IGF-I gene upstream of said IGF-I gene with or without a linker.

(1) Construction of an expression vector for the protein/peptide LH gene

The protein/peptide LH gene is inserted into a plasmid containing a promoter gene, and protein/peptide LH gene is transformed into a host organism.

In a suitable embodiment of this invention, the following recombinant plasmid was established to express protein/peptide LH gene in *E. coli*.

Trp promoter II plasmid pTrpEB7 was digested with EcoRI and BamHI. The resulting large fragment (4.1 kbp) was separated by agarose gel electrophoresis. On the other hand, protein/peptide LH gene was isolated from plasmid pLH107, and ligated with the above promoter vector (4.1 kbp). The mixture was transformed into E. coli HB101. The plasmid was isolated from one of the ampicillin resistant and tetracycline sensitive transformants obtained, and confirmed to contain protein/peptide LH gene by digestion with restriction enzyme and electrophoresis. The thus obtained plasmid was named plasmid pLHtrp. This process is shown in FIG. 13.

(2) Construction of an expression vector for IGF-I fused with protein/peptide LH The IGF-I gene is inserted into a plasmid containing a protein/peptide LH gene downstream of and adjacent to a promoter gene.

In a suitable embodiment of this invention, the following recombinant plasmid was established to express IGF-I fused with protein/peptide LH gene in *E. coli*. In this stage, three types of linker were inserted upstream of and adjacent to the IGF-I gene.

(a) Construction of expression vector for a gene coding for IGF-I fused with protein/peptide LH (Type I)

Plasmid pLHtrp prepared above was digested with HindIII and BamHI. The resultant large fragment was separated by preparative agarose gel electrophoresis. On the other hand, the IGF-I gene was isolated from plasmid pSdMl prepared above with EcoRI and BamHI digestion and oligonucleotides ml and m2 were ligated upstream of and adjacent to it as a linker. The thus obtained IGF-I gene with linker was ligated with the above large fragment of plasmid pLHtrp. The mixture was then transformed into *E. coli* HB101. The plasmid was isolated from one of the ampicillin resistant and tetracycline sensitive transformants obtained, and confirmed to contain a gene coding for IGF-I fused with protein/peptide LH (Type I) by digestion with restriction enzyme and electrophoresis. The thus obtained plasmid was named as plasmid pLHSdMmtrp. This process is shown in FIG. 14.

The sequence of the thus obtained gene coding for IGF-I fused with protein/peptide LH (Type I) is as follows:

```
                    1
        EcoRI  Met  Cys  Tyr  Cys  Gln
Coding:    5'-AATTC—ATG—TGT—TAC—TGC—CAG—
Noncoding:     3'-G—TAC—ACA—ATG—ACG—GTC—

10
Asp  Pro  Tyr  Val  Lys  Glu  Ala  Glu
GAC—CCA—TAT—GTA—AAA—GAA—GCA—GAA—
CTG—GGT—ATA—CAT—TTT—CTT—CGT—CTT—

20
Asn  Leu  Lys  Lys  Tyr  Phe  Asn  Ala
AAC—CTT—AAG—AAA—TAC—TTT—AAT—GCA—
TTG—GAA—TTC—TTT—ATG—AAA—TTA—CGT—

Gly  His  Ser  Asp  Val  Ala  Asp  Asn
GGT—CAT—TCA—GAT—GTA—GCG—GAT—AAT—
CCA—GTA—AGT—CTA—CAT—CGC—CTA—TTA—

30
Gly  Thr  Leu  Phe  Leu  Gly  Ile  Leu
GGA—ACT—CTT—TTC—TTA—GGC—ATT—TTG—
CCT—TGA—GAA—AAG—AAT—CCG—TAA—AAC—

40
Lys  Asn  Trp  Lys  Glu  Glu  Ser  Asp
AAG—AAT—TGG—AAA—GAG—GAG—AGT—GAC—
TTC—TTA—ACC—TTT—CTC—CTC—TCA—CTG—

50
Arg  Lys  Ile  Met  gln  Ser  Gln  Ile
AGA—AAA—ATA—ATG—CAG—AGC—CAA—ATT—
TCT—TTT—TAT—TAC—GTC—TCG—GTT—TAA—

HindIII    60
Val  Ser  Phe  Tyr  Phe  Lys   Leu  Glu
GTC—TCC—TTT—TAC—TTC—AAG—CTT—GAA—
CAG—AGG—AAA—ATG—AAG—TTC—GAA—CTT—

Val  Lys  His  Glu  Phe  Met  Gly  Pro
GTA—AAA—CAT—GAA—TTC—ATG—GGT—CCT—
CAT—TTT—GTA—CTT—AAG—TAC—CCA—GGA—

70
Glu  Thr  Leu  Cys  Gly  Ala  Glu  Leu
GAA—ACT—CTG—TGC—GGC—GCT—GAA—CTG—
CTT—TGA—GAC—ACG—CCG—CGA—CTT—GAC—

80
Val  Asp  Ala  Leu  Gln  Phe  Val  Cys
GTT—GAC—GCT—CTG—CAA—TTT—GTA—TGT—
CAA—CTG—CGA—GAC—GTT—AAA—CAT—ACA—

90
Gly  Asp  Arg  Gly  Phe  Tyr  Phe  Asn
GGT—GAT—CGT—GGT—TTC—TAC—TTC—AAC—
CCA—CTA—GCA—CCA—AAG—ATG—AAG—TTG—

100
Lys  Pro  Thr  Gly  Tyr  Gly  Ser  Ser
AAA—CCG—ACC—GGC—TAT—GGC—TCC—AGC—
TTT—GGC—TGG—CCG—ATA—CCG—AGG—TCG—

Ser  Arg  Arg  Ala  Pro  Gln  Thr  Gly
TCT—CGT—CGC—GCA—CCG—CAG—ACT—GGT—
AGA—GCA—GCG—CGT—GGC—GTC—TGA—CCA—

110
Ile  Val  Asp  Glu  Cys  Cys  Phe  Arg
ATC—GTA—GAC—GAA—TGC—TGT—TTT—CGT—
TAG—CAT—CTG—CTT—ACG—ACA—AAA—GCA—

120
Ser  Cys  Asp  Leu  Arg  Arg  Leu  Glu
TCT—TGC—GAT—CTC—CGC—CGT—CTG—GAA—
AGA—ACG—CTA—GAG—GCG—GCA—GAC—CTT—

130
Met  Tyr  Cys  Ala  Pro  Leu  Lys  Pro
ATG—TAC—TGT—GCT—CCA—CTG—AAG—CCA—
TAC—ATG—ACA—CGA—GGT—GAC—TTC—GGT—

Ala  Lys  Ser  Ala  Stop  stop BamHI
GCA—AAA—TCC—GCG—TGA—TAG-3'
CGT—TTT—AGG—CGC—ACT—ATC—CTAG-5', and
``` the sequence for the gene coding for IGF-I fused with protein/peptide LH (Type I) is as follows:

```
          1
          Cys  Tyr  Cys  Gln  Asp  Pro
Coding:    TGT—TAC—TGC—CAG—GAC—CCA—
Noncoding: ACA—ATG—ACG—GTC—CTG—GGT—

10
Tyr  Val  Lys  Glu  Ala  Glu  Asn  Leu
TAT—GTA—AAA—GAA—GCA—GAA—AAC—CTT—
ATA—CAT—TTT—CTT—CGT—CTT—TTG—GAA—

20
Lys  Lys  Tyr  Phe  Asn  Ala  Gly  His
AAG—AAA—TAC—TTT—AAT—GCA—GGT—CAT—
TTC—TTT—ATG—AAA—TTA—CGT—CCA—GTA—

30
Ser  Asp  Val  Ala  Asp  Asn  Gly  Thr
TCA—GAT—GTA—GCG—GAT—AAT—GGA—ACT—
AGT—CTA—CAT—CGC—CTA—TTA—CCT—TGA—

Leu  Phe  Leu  Gly  Ile  Leu  Lys  Asn
CTT—TTC—TTA—GGC—ATT—TTG—AAG—AAT—
GAA—AAG—AAT—CCG—TAA—AAC—TTC—TTA—

40
Trp  Lys  Glu  Glu  Ser  Asp  Arg  Lys
TGG—AAA—GAG—GAG—AGT—GAC—AGA—AAA—
ACC—TTT—CTC—CTC—TCA—CTG—TCT—TTT—

50
Ile  Met  gln  Ser  Gln  Ile  Val  Ser
ATA—ATG—CAG—AGC—CAA—ATT—GTC—TCC—
TAT—TAC—GTC—TCG—GTT—TAA—CAG—AGG—

HindIII   60
Phe  Tyr  Phe  Lys  Leu  Glu  Val  Lys
TTT—TAC—TTC—AAG—CTT—GAA—GTA—AAA—
AAA—ATG—AAG—TTC—GAA—CTT—CAT—TTT—

70
His  Glu  Phe  Met  Gly  Pro  Glu  Thr
CAT—GAA—TTC—ATG—GGT—CCT—GAA—ACT—
GTA—CTT—AAG—TAC—CCA—GGA—CTT—TGA—

Leu  Cys  Gly  Ala  Glu  Leu  Val  Asp
CTG—TGC—GGC—GCT—GAA—CTG—GTT—GAC—
GAC—ACG—CCG—CGA—CTT—GAC—CAA—CTG—

80
Ala  Leu  Gln  Phe  Val  Cys  Gly  Asp
GCT—CTG—CAA—TTT—GTA—TGT—GGT—GAT—
CGA—GAC—GTT—AAA—CAT—ACA—CCA—CTA—

90
Arg  Gly  Phe  Tyr  Phe  Asn  Lys  Pro
CGT—GGT—TTC—TAC—TTC—AAC—AAA—CCG—
GCA—CCA—AAG—ATG—AAG—TTG—TTT—GGC—

100
Thr  Gly  Tyr  Gly  Ser  Ser  Ser  Arg
ACC—GGC—TAT—GGC—TCC—AGC—TCT—CGT—
TGG—CCG—ATA—CCG—AGG—TCG—AGA—GCA—

110
Arg  Ala  Pro  Gln  Thr  Gly  Ile  Val
CGC—GCA—CCG—CAG—ACT—GGT—ATC—GTA—
GCG—CGT—GGC—GTC—TGA—CCA—TAG—CAT—

Asp  Glu  Cys  Cys  Phe  Arg  Ser  Cys
GAC—GAA—TGC—TGT—TTT—CGT—TCT—TGC—
CTG—CTT—ACG—ACA—AAA—GCA—AGA—ACG—
```

```
                    120
Asp   Leu   Arg   Arg   Leu   Glu   Met   Tyr
GAT—CTC—CGC—CGT—CTG—GAA—ATG—TAC—
CTA—GAG—GCG—GCA—GAC—CTT—TAC—ATG—

130
Cys   Ala   Pro   Leu   Lys   Pro   Ala   Lys
TGT—GCT—CCA—CTG—AAG—CCA—GCA—AAA—
ACA—CGA—GGT—GAC—TTC—GGT—CGT—TTT—

Ser   Ala
TCC—GCG-3'
AGG—CGC-5'
```

(b) Construction of an expression vector for a gene coding for IGF-I fused with protein/peptide LH (Type II)

A plasmid pLHtrp prepared as set out above was digested with HindIII and BamHI. The resultant large fragment was separated by preparative agarose gel electrophoresis. On the other hand, the IGF-I gene was isolated from plasmid pSdMl prepared above with AvaII and BamHI, and oligonucleotides LA and LB were ligated upstream of and adjacent to it as a linker. The thus obtained IGF-I gene with linker was ligated with the above large fragment of plasmid pLHtrp. The mixture was transformed into *E. coli* HB101. The plasmid was isolated from one of the ampicillin resistant and tetracycline sensitive transformants obtained, and confirmed to contain a gene coding for IGF-I fused with protein/peptide LH (Type II) by digestion with restriction enzyme and electrophoresis. The thus obtained plasmid was named as plasmid pLHSdMwtrp. This process is shown in FIG. 15 and FIG. 16.

The sequence of the thus obtained gene coding for IGF-I fused with protein/peptide LH (Type II) is as follows;

```
                 1
           EcoRI   Met   Cys   Tyr   Cys   Gln
Coding:    5'-AATTC—ATG—TGT—TAC—TGC—CAG—
Noncoding:      3'-G—TAC—ACA—ATG—ACG—GTC—

10
Asp   Pro   Tyr   Val   Lys   Glu   Ala   Glu
GAC—CCA—TAT—GTA—AAA—GAA—GCA—GAA—
CTG—GGT—ATA—CAT—TTT—CTT—CGT—CTT—

20
Asn   Leu   Lys   Lys   Tyr   Phe   Asn   Ala
AAC—CTT—AAG—AAA—TAC—TTT—AAT—GCA—
TTG—GAA—TTC—TTT—ATG—AAA—TTA—CGT—

Gly   His   Ser   Asp   Val   Ala   Asp   Asn
GGT—CAT—TCA—GAT—GTA—GCG—GAT—AAT—
CCA—GTA—AGT—CTA—CAT—CGC—CTA—TTA—

30
Gly   Thr   Leu   Phe   Leu   Gly   Ile   Leu
GGA—ACT—CTT—TTC—TTA—GGC—ATT—TTG—
CCT—TGA—GAA—AAG—AAT—CCG—TAA—AAC—

40
Lys   Asn   Trp   Lys   Glu   Glu   Ser   Asp
AAG—AAT—TGG—AAA—GAG—GAG—AGT—GAC—
TTC—TTA—ACC—TTT—CTC—CTC—TCA—CTG—

50
Arg   Lys   Ile   Met   gln   Ser   Gln   Ile
AGA—AAA—ATA—ATG—CAG—AGC—CAA—ATT—
TCT—TTT—TAT—TAC—GTC—TCG—GTT—TAA—

HindIII        60
Val   Ser   Phe   Tyr   Phe   Lys   Leu   Glu
GTC—TCC—TTT—TAC—TTC—AAG—CTT—GAA—
CAG—AGG—AAA—ATG—AAG—TTC—GAA—CTT—

Val   Trp   Gly   Pro   Glu   Thr   Leu   Cys
GTA—TGG—GGT—CCT—GAA—ACT—CTG—TGC—
CAT—ACC—CCA—GGA—CTT—TGA—GAC—ACG—

70
Gly   Ala   Glu   Leu   Val   Asp   Ala   Leu
GGC—GCT—GAA—CTG—GTT—GAC—GCT—CTG—
CCG—CGA—CTT—GAC—CAA—CTG—CGA—GAC—

80
Gln   Phe   Val   Cys   Gly   Asp   Arg   Gly
CAA—TTT—GTA—TGT—GGT—GAT—CGT—GGT—
GTT—AAA—CAT—ACA—CCA—CTA—GCA—CCA—

90
Phe   Tyr   Phe   Asn   Lys   Pro   Thr   Gly
TTC—TAC—TTC—AAC—AAA—CCG—ACC—GGC—
AAG—ATG—AAG—TTG—TTT—GGC—TGG—CCG—

100
Tyr   Gly   Ser   Ser   Ser   Arg   Arg   Ala
TAT—GGC—TCC—AGC—TCT—CGT—CGC—GCA—
ATA—CCG—AGG—TCG—AGA—GCA—GCG—CGT—

Pro   Gln   Thr   Gly   Ile   Val   Asp   Glu
CCG—CAG—ACT—GGT—ATC—GTA—GAC—GAA—
GGC—GTC—TGA—CCA—TAG—CAT—CTG—CTT—

110
Cys   Cys   Phe   Arg   Ser   Cys   Asp   Leu
TGC—TGT—TTT—CGT—TCT—TGC—GAT—CTC—
ACG—ACA—AAA—GCA—AGA—ACG—CTA—GAG—

120
Arg   Arg   Leu   Glu   Met   Tyr   Cys   Ala
CGC—CGT—CTG—GAA—ATG—TAC—TGT—GCT—
GCG—GCA—GAC—CTT—TAC—ATG—ACA—CGA—

130
Pro   Leu   Lys   Pro   Ala   Lys   Ser   Ala
CCA—CTG—AAG—CCA—GCA—AAA—TCC—GCG—
GGT—GAC—TTC—GGT—CGT—TTT—AGG—CGC—

Stop    stop  BamHI
TGA—TAG-3'
ACT—ATC—CTAG-5', and
``` the sequence of the gene coding for IGF-I fused with protein/peptide LH (Type II) is as follows:

```
                 1
           Cys   Tyr   Cys   Gln   Asp   Pro
Coding:    5'-TGT—TAC—TGC—CAG—GAC—CCA—
Noncoding: 3'-ACA—ATG—ACG—GTC—CTG—GGT—

10
Tyr   Val   Lys   Glu   Ala   Glu   Asn   Leu
TAT—GTA—AAA—GAA—GCA—GAA—AAC—CTT—
ATA—CAT—TTT—CTT—CGT—CTT—TTG—GAA—

20
Lys   Lys   Tyr   Phe   Asn   Ala   Gly   His
AAG—AAA—TAC—TTT—AAT—GCA—GGT—CAT—
TTC—TTT—ATG—AAA—TTA—CGT—CCA—GTA—

30
Ser   Asp   Val   Ala   Asp   Asn   Gly   Thr
TCA—GAT—GTA—GCG—GAT—AAT—GGA—ACT—
AGT—CTA—CAT—CGC—CTA—TTA—CCT—TGA—

Leu   Phe   Leu   Gly   Ile   Leu   Lys   Asn
CTT—TTC—TTA—GGC—ATT—TTG—AAG—AAT—
GAA—AAG—AAT—CCG—TAA—AAC—TTC—TTA—
```

```
                    40
Trp  Lys  Glu  Glu  Ser  Asp  Arg  Lys
TGG—AAA—GAG—GAG—AGT—GAC—AGA—AAA—
ACC—TTT—CTC—CTC—TCA—CTG—TCT—TTT—

50
Ile  Met  Gln  Ser  Gln  Ile  Val  Ser
ATA—ATG—CAG—AGC—CAA—ATT—GTC—TCC—
TAT—TAC—GTC—TCG—GTT—TAA—CAG—AGG—

HindIII    60
Phe  Tyr  Phe  Lys  Leu  Glu  Val  Trp
TTT—TAC—TTC—AAG—CTT—GAA—GTA—TGG—
AAA—ATG—AAG—TTC—GAA—CTT—CAT—ACC—

70
Gly  Pro  Glu  Thr  Leu  Cys  Gly  Ala
GGT—CCT—GAA—ACT—CTG—TGC—GGC—GCT—
CCA—GGA—CTT—TGA—GAC—ACG—CCG—CGA—

Glu  Leu  Val  Asp  Ala  Leu  Gln  Phe
GAA—CTG—GTT—GAC—GCT—CTG—CAA—TTT—
CTT—GAC—CAA—CTG—CGA—GAC—GTT—AAA—

80
Val  Cys  Gly  Asp  Arg  Gly  Phe  Tyr
GTA—TGT—GGT—GAT—CGT—GGT—TTC—TAC—
CAT—ACA—CCA—CTA—GCA—CCA—AAG—ATG—

90
Phe  Asn  Lys  Pro  Thr  Gly  Tyr  Gly
TTC—AAC—AAA—CCG—ACC—GGC—TAT—GGC—
AAG—TTG—TTT—GGC—TGG—CCG—ATA—CCG—

100
Ser  Ser  Ser  Arg  Arg  Ala  Pro  Gln
TCC—AGC—TCT—CGT—CGC—GCA—CCG—CAG—
AGG—TCG—AGA—GCA—GCG—CGT—GGC—GTC—

110
Thr  Gly  Ile  Val  Asp  Glu  Cys  Cys
ACT—GGT—ATC—GTA—GAC—GAA—TGC—TGT—
TGA—CCA—TAG—CAT—CTG—CTT—ACG—ACA—

Phe  Arg  Ser  Cys  Asp  Leu  Arg  Arg
TTT—CGT—TCT—TGC—GAT—CTC—CGC—CGT—
AAA—GCA—AGA—ACG—CTA—GAG—GCG—GCA—

120
Leu  Glu  Met  Tyr  Cys  Ala  Pro  Leu
CTG—GAA—ATG—TAC—TGT—GCT—CCA—CTG—
GAC—CTT—TAC—ATG—ACA—CGA—GGT—GAC—

130
Lys  Pro  Ala  Lys  Ser  Ala
AAG—CCA—GCA—AAA—TCC—GCG
TTC—GGT—CGT—TTT—AGG—CGC
```

(c) Construction of expression vector of a gene coding for IGF-I fused with protein/peptide LH (Type III)

A plasmid pLHtrp prepared as set out above was digested with HindIII and BamHI. The resultant large fragment was separated by preparative agarose gel electrophoresis. On the other hand, an IGF-I gene was isolated from plasmid pSdM1 prepared above with AvaII and BamHI, and oligonucleotides LC and LD were ligated upstream of and adjacent to it as a linker. The thus obtained IGF-I with linker was ligated with the large fragment of plasmid pBR322 digested with EcoRI and BamHI. The thus obtained plasmid pSdMc was cloned using *E. coli* and then digested again with EcoRI and BamHI. The thus obtained IGF-I gene with a linker was ligated with the linker m1 and m2 using a protocol similar to that used for the Type I expression vector. Finally the IGF-I gene obtained with two linkers was ligated the above large fragment of plasmid pLHtrp. The mixture was transformed into *E. coli* HB101. The plasmid was isolated from one of the ampicillin resistant and tetracycline sensitive transformants obtained, and confirmed to contain a gene coding for IGF-I fused with protein/peptide LH (Type III) by digestion with restriction enzyme and electrophoresis. The thus obtained plasmid was named as plasmid pLHSdMctrp. This process is shown in FIG. 17 and FIG. 18.

The sequence of the thus obtained gene coding for IGF-I fused with protein/peptide LH (Type III) is as follows:

```
               1
         EcoRI    Met   Cys   Tyr   Cys   Gln   Asp   Pro   Tyr
Coding:   5'-AATTC—ATG—TGT—TAC—TGC—CAG—GAC—CCA—TAT—

Noncoding:   3'-G—TAC—ACA—ATG—ACG—GTC—CTG—GGT—ATA—

10                                              20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                    HindIII 60
Ser  Gln  Ile  Val  Ser  Phe  Tyr  Phe  Lys  Leu  Glu  Val  Lys  His—
AGC—CAA—ATT—GTC—TCC—TTT—TAC—TTC—AAG—CTT—GAA—GTA—AAA—CAT—
TCG—GTT—TAA—CAG—AGG—AAA—ATG—AAG—TTC—GAA—CTT—CAT—TTT—GTA—

Glu  Phe  Gly  Pro  Ala
GAA—TTC—GGC—CCC—GCG—
CTT—AAG—CCG—GGG—CGC—
```

```
                    70
Gly  Pro  Glu  Thr  Leu  Cys  Gly  Ala  Glu  Leu  Val
GGT—CCT—GAA—ACT—CTG—TGC—GGC—GCT—GAA—CTG—GTT—
CCA—GGA—CTT—TGA—GAC—ACG—CCG—CGA—CTT—GAC—CAA—

80                                  90
Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

100
Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

110                                  120
Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

130
Leu  Arg  Arg  Leu  Glu  Met  Tyr  Cys  Ala  Pro  Leu  Lys  Pro  Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT—

Lys  Ser  Ala  Stop  stop  BamHI
AAA—TCC—GCG—TGA—TAG-3'
TTT—AGG—CGC—ACT—ATC—CTAG-5', and
``` the sequence for the gene coding for IGF-I fused with protein/peptide LH (Type III) is as follows:

```
         1
          Cys  Tyr  Cys  Gln  Asp  Pro
Coding:    5'-TGT—TAC—TGC—CAG—GAC—CCA—
Noncoding: 3'-ACA—ATG—ACG—GTC—CTG—GGT—

10
Tyr  Val  Lys  Glu  Ala  Glu  Asn  Leu
TAT—GTA—AAA—GAA—GCA—GAA—AAC—CTT—
ATA—CAT—TTT—CTT—CGT—CTT—TTG—GAA—

20
Lys  Lys  Tyr  Phe  Asn  Ala  Gly  His
AAG—AAA—TAC—TTT—AAT—GCA—GGT—CAT—
TTC—TTT—ATG—AAA—TTA—CGT—CCA—GTA—

30
Ser  Asp  Val  Ala  Asp  Asn  Gly  Thr
TCA—GAT—GTA—GCG—GAT—AAT—GGA—ACT—
AGT—CTA—CAT—CGC—CTA—TTA—CCT—TGA—

Leu  Phe  Leu  Gly  Ile  Leu  Lys  Asn
CTT—TTC—TTA—GGC—ATT—TTG—AAG—AAT—
GAA—AAG—AAT—CCG—TAA—AAC—TTC—TTA—

40
Trp  Lys  Glu  Glu  Ser  Asp  Arg  Lys
TGG—AAA—GAG—GAG—AGT—GAC—AGA—AAA—
ACC—TTT—CTC—CTC—TCA—CTG—TCT—TTT—

50
Ile  Met  Gln  Ser  Gln  Ile  Val  Ser
ATA—ATG—CAG—AGC—CAA—ATT—GTC—TCC—
TAT—TAC—GTC—TCG—GTT—TAA—CAG—AGG—

HindIII     60
Phe  Tyr  Phe  Lys  Leu  Glu  Val  Lys
TTT—TAC—TTC—AAG—CTT—GAA—GTA—AAA—
AAA—ATG—AAG—TTC—GAA—CTT—CAT—TTT—

70
His  Glu  Phe  Gly  Pro  Ala  Gly  Pro
CAT—GAA—TTC—GGC—CCC—GCG—GGT—CCT—
GTA—CTT—AAG—CCG—GGG—CGC—CCA—GGA—

Glu  Thr  Leu  Cys  Gly  Ala  Glu  Leu
GAA—ACT—CTG—TGC—GGC—GCT—GAA—CTG—
CTT—TGA—GAC—ACG—CCG—CGA—CTT—GAC—

80
Val  Asp  Ala  Leu  Gln  Phe  Val  Cys
GTT—GAC—GCT—CTG—CAA—TTT—GTA—TGT—
CAA—CTG—CGA—GAC—GTT—AAA—CAT—ACA—

90
Gly  Asp  Arg  Gly  Phe  Tyr  Phe  Asn
GGT—GAT—CGT—GGT—TTC—TAC—TTC—AAC—
CCA—CTA—GCA—CCA—AAG—ATG—AAG—TTG—

100
Lys  Pro  Thr  Gly  Tyr  Gly  Ser  Ser
AAA—CCG—ACC—GGC—TAT—GGC—TCC—AGC—
TTT—GGC—TGG—CCG—ATA—CCG—AGG—TCG—

110
Ser  Arg  Arg  Ala  Pro  Gln  Thr  Gly
TCT—CGT—CGC—GCA—CCG—CAG—ACT—GGT—
AGA—GCA—GCG—CGT—GGC—GTC—TGA—CCA—

Ile  Val  Asp  Glu  Cys  Cys  Phe  Arg
ATC—GTA—GAC—GAA—TGC—TGT—TTT—CGT—
TAG—CAT—CTG—CTT—ACG—ACA—AAA—GCA—

120
Ser  Cys  Asp  Leu  Arg  Arg  Leu  Glu
TCT—TGC—GAT—CTC—CGC—CGT—CTG—GAA—
AGA—ACG—CTA—GAG—GCG—GCA—GAC—CTT—

130
Met  Tyr  Cys  Ala  Pro  Leu  Lys  Pro
ATG—TAC—TGT—GCT—CCA—CTG—AAG—CCA—
TAC—ATG—ACA—CGA—GGT—GAC—TTC—GGT—

Ala  Lys  Ser  Ala  Stop   stop BamHI
GCA—AAA—TCC—GCG—TGA—TAG-3'
CGT—TTT—AGG—CGC—ACT—ATC—CTAG-5'
```

[5] Expression of the IGF-I gene in a host organism

For the expression of the IGF-I gene, the thus obtained plasmid having a promoter gene and an IGF-I gene is transformed into a host organism. Then the host organism having the plasmid is the cultured in a nutrient medium containing sources of assimilable carbon and nitrogen under aerobic conditions (e.g. shaking culture, submerged culture, etc.).

The preferred sources of carbon in the nutrient medium are carbohydrates such as glucose, fructose, sucrose, glycerin, starch and the like. Other sources which may be included are xylose, galactose, maltose, dextrin, lactose and the like.

The preferred sources of nitrogen are yeast extract, peptone, gluten meal, cottonseed flour, soybean meal, corn steep liquor, dried yeast, wheat germ, etc., as well as inorganic and organic nitrogen compounds such as ammonium nitrate, ammonium sulfate, ammonium phosphate, etc.), urea, amino acid and the like.

The carbon and nitrogen sources, though advantageously employed in combination, need not be used in their pure form, because less pure materials which contain traces of growth factors and considerable quantities of mineral nutrients, are also suitable for use. When desired, mineral salts such as calcium carbonate, sodium or potassium phosphate, sodium or potassium chloride, magnesium salts, copper salts and the like may be added to the culture medium.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Agitation may be effected by passing sterile air through the fermentation mixture.

The fermentation is usually conducted at a temperature between about 20° C. and 42° C., preferably 35°-38° C., for a period of several hours to 50 hours.

The thus produced IGF-I or fused IGF-I can be recovered from the cultured medium by conventional means which are commonly used for the recovery of other known biologically active substances. In genera, the IGF-I or fused IGF-I produced is found in the cells of the host organisms. Accordingly IGF-I or fused IGF-I can be separated from the cells, which are obtained by filtering or centrifuging the cultured broth, by a conventional method such as concentration under reduced pressure, lysis such as sonication, HPLC, lyophilization, pH adjustment, treatment with resin (e.g. anion or cation exchange resin, non-ionic adsorption resin), treatment with a conventional adsorbent (e.g. activated carbon, silicic acid, silica gel, cellulose, almina), gel filtration, crystallization, and the like.

(1) Expression of the IGF-I gene in *E. coli* using plasmid pSdMltrp

An overnight culture of *E. coli* HB101 containing pSdMltrp in L broth was diluted in M9 medium lacking tryptophan, and the cells were incubated at 37° C. for 3 hours under the condition of β-indoleacrylic acid induction. Detection of IGF-I production was carried out using a radioimmunoassay (hereinafter referred to as RIA) with the antibody of IGF-I fragment (26–46) using N. Yanaihara's method [N. Yanaihara et al, Peptide Hormones in Pancreas 3, 28(1983)].

(2) Expression of the IGF-I gene in *E. coli* using plasmid pSdMl-322trp

An overnight culture of *E. coli* HB101 containing plasmid pSdMl-322trp in L broth was diluted in M9 medium lacking tryptophan, and the cells were incubated at 37° C. for 3 hours under the condition of β-indoleacrylic acid induction. Detection of IGF-I production was carried out using RIA with the antibody of IGF-I fragment (26–46) using N. Yanaihara's method.

[5] Expression of a gene coding for fused IGF-I in a host organism (1) Expression of a gene coding for IGF-I gene fused with protein/peptide LH (Type I) in a host organism For the expression of a gene coding, for IGF-I fused with protein/peptide LH (Type I), the thus obtained plasmid having a promoter gene and a gene coding for IGF-I fused with protein/peptide LH (Type I) is transformed into a host organism. Then the host organism having the plasmid is cultured in a suitable medium. IGF-I fused with protein/peptide LH (Type I) is isolated from the resulting culture broth.

(i) Expression of a gene coding for IGF-I fused with protein/peptide LH (Type I) in *E. coli* using plasmid pLHSdMmtrp An overnight culture of *E. coli* HB101 containing pLHSdMmtrp in L broth was diluted in M9 medium lacking tryptophan, and the cells were incubated at 37° C. for 3 hours under the condition of β-indoleacrylic acid induction. Detection of production of the fused IGF-I was carried out using a radioimmunoassay (hereinafter referred to as RIA) with the antibody of IGF-I fragment (26–46) using N. Yanaihara's method [N. Yanaihara et al, Peptide Hormones in Pancreas 3, 28(1983)].

(ii) Isolation of IGF-I fused with protein/peptide LH (Type I)

The culture fluid was centrifuged to give a wet cell paste, and the cells were lysed by sonication. The pellet was collected by centrifugation and then dissolved in 8M urea solution containing 0.1 M dithiothreitol (hereinafter referred to as DTT). After centrifugation the solution was purified by S 300 column chromatography. Active fractions detected by RIA were collected and dialysed to give protein which contains the desired component. The fused IGF-I was detected its normal position (15500) on polyacrylamide gel electrophoresis.

The sequence of the thus obtained IGF-I fused with protein/peptide LH (Type I) is as follows

```
1                                                    10
Cys—Tyr—Cys—Gln—Asp—Pro—Tyr—Val—Lys—Glu—

20
Ala—Glu—Asn—Leu—Lys—Lys—Tyr—Phe—Asn—Ala—

30
Gly—His—Ser—Asp—Val—Ala—Asp—Asn—Gly—Thr—

40
Leu—Phe—Leu—Gly—Ile—Leu—Lys—Asn—Trp—Lys—

50
Glu—Glu—Ser—Asp—Arg—Lys—Ile—Met—Gln—Ser—

60
Gln—Ile—Val—Ser—Phe—Tyr—Phe—Lys—Leu—Glu—

70
Val—Lys—His—Glu—Phe—Met—Gly—Pro—Glu—Thr—

80
Leu—Cys—Gly—Ala—Glu—Leu—Val—Asp—Ala—Leu—

90
Gln—Phe—Val—Cys—Gly—Asp—Arg—Gly—Phe—Tyr—

100
Phe—Asn—Lys—Pro—Thr—Gly—Tyr—Gly—Ser—Ser—
```

-continued

```
                                          110
Ser—Arg—Arg—Ala—Pro—Gln—Thr—Gly—Ile—Val—

120
Asp—Glu—Cys—Cys—Phe—Arg—Ser—Cys—Asp—Leu—

130
Arg—Arg—Leu—Glu—Met—Tyr—Cys—Ala—Pro—Leu—

Lys—Pro—Ala—Lys—Ser—Ala
```

(2) Expression of a gene coding for IGF-I fused with protein/peptide LH (Type II) in a host organism:

(i) Expression of a gene coding for IGF-I fused with protein/peptide LH (Type II) in *E. coli* using plasmid pLHSdMwtrp This process can be conducted using a protocol similar to that used for the expression of a gene coding for IGF-I fused with protein/peptide LH (Type I).

(ii) Isolation of IGF-I fused with protein/peptide LH (Type II)

This process can be conducted using a protocol similar to that used for the isolation of IGF-I fused with protein/peptide LH (Type I).

The thus obtained IGF-I fused with protein/peptide LH (Type II) is as follows:

```
1                                         10
Cys—Tyr—Cys—Gln—Asp—Pro—Tyr—Val—Lys—Glu—

20
Ala—Glu—Asn—Leu—Lys—Lys—Tyr—Phe—Asn—Ala—

30
Gly—His—Ser—Asp—Val—Ala—Asp—Asn—Gly—Thr—

40
Leu—Phe—Leu—Gly—Ile—Leu—Lys—Asn—Trp—Lys—

50
Glu—Glu—Ser—Asp—Arg—Lys—Ile—Met—Gln—Ser—

60
Gln—Ile—Val—Ser—Phe—Tyr—Phe—Lys—Leu—Glu—

70
Val—Trp—Gly—Pro—Glu—Thr—Leu—Cys—Gly—Ala—

80
Glu—Leu—Val—Asp—Ala—Leu—Gln—Phe—Val—Cys—

90
Gly—Asp—Arg—Gly—Phe—Tyr—Phe—Asn—Lys—Pro—

100
Thr—Gly—Tyr—Gly—Ser—Ser—Ser—Arg—Arg—Ala—

110
Pro—Gln—Thr—Gly—Ile—Val—Asp—Glu—Cys—Cys—

120
Phe—Arg—Ser—Cys—Asp—Leu—Arg—Arg—Leu—Glu—

130
Met—Tyr—Cys—Ala—Pro—Leu—Lys—Pro—Ala—Lys—

Ser—Ala
```

(3) Expression of a gene coding for IGF-I fused with protein/peptide LH (Type III) in a host organism (i) Expression of a gene coding for IGF-I fused with protein/peptide LH (Type III) in *E. coli* using plasmid pLHSdMctrp This process can be conducted using a protocol similar manner to that used for the expression of a gene coding for IGF-I fused with protein/peptide LH (Type I).

(ii) Isolation of IGF-I fused with protein/peptide LH (Type III)

This process can be conducted using a protocol similar to that used for the isolation of IGF-I fused with protein/peptide LH (Type I).

The thus obtained IGF-I fused with protein/peptide LH (Type III) is as follows:

```
1                                         10
Cys—Tyr—Cys—Gln—Asp—Pro—Tyr—Val—Lys—Glu—

20
Ala—Glu—Asn—Leu—Lys—Lys—Tyr—Phe—Asn—Ala—

30
Gly—His—Ser—Asp—Val—Ala—Asp—Asn—Gly—Thr—

40
Leu—Phe—Leu—Gly—Ile—Leu—Lys—Asn—Trp—Lys—

50
Glu—Glu—Ser—Asp—Arg—Lys—Ile—Met—Gln—Ser—

60
Gln—Ile—Val—Ser—Phe—Tyr—Phe—Lys—Leu—Glu—

70
Val—Lys—His—Glu—Phe—Gly—Pro—Ala—Gly—Pro—

80
Glu—Thr—Leu—Cys—Gly—Ala—Glu—Leu—Val—Asp—

90
Ala—Leu—Gln—Phe—Val—Cys—Gly—Asp—Arg—Gly—

100
Phe—Tyr—Phe—Asn—Lys—Pro—Thr—Gly—Tyr—Gly—

110
Ser—Ser—Ser—Arg—Arg—Ala—Pro—Gln—Thr—Gly—

120
Ile—Val—Asp—Glu—Cys—Cys—Phe—Arg—Ser—Cys—

130
Asp—Leu—Arg—Arg—Leu—Glu—Met—Tyr—Cys—Ala—

Pro—Leu—Lys—Pro—Ala—Lys—Ser—Ala
```

[7] Conversion of fused IGF-I to IGF-I and isolation of IGF-I:

The thus obtained fused IGF-I can be converted to IGF-I by cleaving the protective peptide.

This cleavage reaction can be conducted in accordance with conventional method used in the field of peptide chemistry. Suitable cleavage reaction can be selected according to the type of fused IGF-I.

Suitable agent used in this cleavage reaction may include cyanogen bromide; (3-bromo-2-o-nitrophenylsulfenyl)skatole (hereinafter referred to as BNPS-skatole) or N-chlorosuccinimide (hereinafter referred to as NCS); collagenase and the like.

This cleavage reaction is usually carried out under mild conditions in a conventional solvent which does not adversely affect the reaction.

The reaction temperature is not critical and the reaction is usually conducted from cooling to warming.

The cleavage reactions which can be applied to the three most preferable types of fused IGF-I are hereinafter described in detail.

(1) Cleavage of the protein/peptide from IGF-I fused with the protein/peptide a methionine residue of the protein/peptide IGF-I fused with a protein/peptide through methionine residue of the protein/peptide can be converted to IGF-I by cleavage reaction with cyanogen bromide.

In this case, although IGF-I itself has a methionine residue at the 59th position of its amino acid sequence, cleavage at the amide bond linking the 59th methionine and the 60th tyrosine of IGF-I follows the cleavage at the amide bond linking the methionine in front of the 1st amino acid of IGF-I and the 1st amino acid of IGF-I, glycine. This phenomena, the order of cleavage at the bond neighboring methionine has been discovered by the inventors for the first time. According to this phenomena, the protein/peptide can be removed easily by cleavage reaction from the fused IGF-I with cyanogen bromide if the suitable condition are selected.

This reaction is usually carried out under mild conditions in a conventional solvent which does not adversely affect the reaction.

The reaction temperature is not critical and the reaction is usually carried out from cooling to warming.

Cleaving of protein/peptide LH from fused IGF-I with protein/peptide LH a methionine residue of protein peptide LH (Type I):

The fused IGF-I was treated with cyanogen bromide in 60% formic acid at 25° C. for 3 hours. After lyophilization the residue was dissolved in 8 M urea solution containing 50 mM 2-mercaptoethanol and dialyzed to give a crude mixture of reduced IGF-I. The mixture was purified by cationic ion exchange chromatography (CM52), and active fractions detected by RIA were collected and dialysed. The dialysed fraction was applied to high performance liquid chromatography to give a pure reduced IGF-I, The reduced IGF-I was converted to oxidized IGF-I by the usual manner of refolding. The purified IGF-I showed a single band on polyacrylamide gel electrophoresis (PAGE), and the IGF-I was superimposed with authentic IGF-I (gift of Dr. Humbel) on HPLC. The amino acid sequence of IGF-I was determined by a combination of Edman's method the carboxypeptidase method. The IGF-I showed biological activity in [$^3$H]-thymidine incorporation assay of mouse BALB/c 3T3 cells.

(2) Cleavage of the protein/peptide from IGF-I fused with the protein/peptide a tryptophan residue of the protein/peptide IGF-I fused with a protein/peptide through a tryptophan residue of the protein/peptide can be converted to IGF-I by cleavage reaction with BNPS-skatole or N-chlorosuccinimide.

This reaction is usually carried out under mild conditions in a conventional solvent which does not adversely affect the reaction.

The reaction temperature is not critical and the reaction is usually carried out from cooling to warming.

Cleavage of protein/peptide LH from the IGF-I fused with protein/peptide LH through tryptophan residue of protein/peptide LH (Type II)

The fused IGF-I was treated with BNPS-skatole in 70% acetic acid or NCS in urea. After the reaction, the mixture was treated with 2-mercaptoethanol and then purified by reverse phase HPLC (RPSC column) to give IGF-I sulfoxide. The IGF-I sufloxide was treated with 5 M thioglycolic acid at 50° C. After addition of 6 M guanidine and 2-mercaptoethanol, the mixture was purified by reverse phase HPLC (RPSC column) to give a pure reduced IGF-I. The reduced IGF-I was identified with that obtained by cleavage reaction of IGF-I fused with protein/peptide LH (Type I).

(3) Cleavage of the protein/peptide from IGF-I fused with the protein/peptide through a '-Gly-Pro-Ala-' sequence of the protein/peptide IGF-I fused with.,the protein/peptide through a '-Gly-Pro-Ala-' sequence of the protein/peptide can be converted to IGF-I by cleavage reaction with collagenase.

The reaction is usually carried out under mild conditions in a conventional solvent which does not adversely affect the reaction.

The reaction temperature is not critical and the reaction is usually carried out from cooling to warming.

Cleavage of protein/peptide LH from IGF-I fused with protein/peptide LH through a '-Gly-Pro-Ala-' sequence of protein/peptide LH (Type III)

The fused IGF-I was treated with collagenase in 2.4 M urea or 2 M guanidine HCl at 30° C. for 18 hours. After addition of DTT to the reaction mixture, it was analyzed by HPLC (RPSC column) to detect a peak corresponding to reduced IGF-I.

[8] Radioimmunoassay of IGF-I

RIA of IGF-I was carried out according to the method established by N. Yanaihara [N. Yanaihara et al: Peptide Hormones in Pancreas 3, 28(1983)]. With 0.1 ml of the above sample or standard sample (IGF-I fragment (26-46)) sample buffer [0.5% BSA in 0.01M PBS, 0.025 M EDTA (pH 7.4) (0.4 ml)], rabbit antiserum (0.1 ml) of IGF-I (26-46) and $^{125}$I-IGF-I (26-46) (0.1 ml) were mixed. The mixture was allowed to stand for 48 hours at 4° C., and then added with rabbit serum (0.1 ml), rabbit γ-globulin antiserum (0.1 ml and 5% PEG6000 (0.9 ml). After standing for additional 2 hours at 4° C. the pellet was collected by centrifugation (3 krpm 4° C., 30 minutes). Radioactivity was measured by γ-counter. The content of IGF-I was calculated from this radioactivity.

[9] Biological assay of IGF-I

Mouse BALB/c 3T3 embryofibroblasts (clone A31) were trypsinized and resuspended at a concentration of $10^5$ cells/ml in Dulbecco-Vogt Modified Eagle's medium containing 10% New Born Calf Serum and 25 mM N-(2-hydroxyethyl)piperazine-N'-2-ethanesulfonic acid (HEPES). Aliquots of 100 ul were plated into 0.3 cm$^2$ wells(96 well-microtiter plate, Costor). Three to four days after the cells reached confluence (5-7 days after initial plating) the sent medium was removed and the culture was washed three times and then 0.2 μCi/well [$^3$H]thymidine (0.67 Ci/mmole) plus test samples were added. After incubation of 24 hours, the medium was removed and cells were washed with PBS and trypsinized for determination of radioactivity. Cells were trapped in glass filters by use of semi automatic multiple cell harvester (LAVO MASH, LABO SCIENCE). Incorporated [$^3$H]thymidine was counted in 8 ml of Aquazol 2 (New England Nuclear) using a Packard Tri-Carb Liquid Scintillation Counter.

The following examples are given for the purpose of illustrating the present invention.

EXAMPLE 1

Synthesis of HOApApApCpCpG-pApCpCpGpGpCpTpApTpGOH (G1)

(1) Synthesis of DMTrOTpoA$^{Bz}$poTpoG$^{iB}$po$^{Ac}$Upo-cellulose i) Preparation of HOG$^{iB}$po$^{Ac}$Upo-cellulose To a suspension of DMTrOG$^{iB}$po$^{Ac}$Upo-cellulose (130.4 mg, 4.59 μmole*) (prepared by R. Crea's method[1])) in methanol/CHCl$_3$ (1:9 v/v, 5.0 ml). TCA/CHCl$_3$ (2:8 w/v, 5.0 ml) was added under ice cooling, and the mixture was stirred at 0° C. for 10 min. After being washed with CHCl$_3$ (2 ml) and methanol (6.0 ml), successively, on the filter, the cellulose adduct (HOG$^{iB}$po$^{Ac}$Upo-cellulose) was dried, water being separated as the pyridine (2 ml) azeotrope.
* This value was calculated by monitoring the absorbance of a washing solution with CHCl$_3$ at 507 nm.

(1) R. Crea et al, Nucleic Acid Res. 8, 2331(1980)

ii) Preparation of DMTrOTpoA$^{Bz}$poTpoi$^-$

DMTrOTpoA$^{Bz}$poTpo-CE (39.9 mg, 23.0 μmole) was treated with Et$_3$N-CH$_3$CN (1:1 v/v, 5 ml) at room temperature for 1 hr. The phosphodiester trimer (DMTrOTpoA$^{Bz}$poTpo$^-$) so obtained was dried, water being separated as the pyridine azeotrope (0.5 ml, 2×1 ml).

iii) Coupling

The trimer (DMTrOTpoA$^{Bz}$poTpo$^-$) *was mixed with the cellulose adduct* (HOG$^{iB}$po$^{Ac}$Upo-cellulose) in a 10 ml round-bottom flask. The mixture was dried, water being separated as the pyridine azeotrope (2×1 ml) and finally resuspended in anhydrous pyridine (1 ml). Mesitylen sulfonyl nitrotriazolide (MSNT) (68.0 mg, 230 μmole) was added to the suspension and the mixture was stirred at room temperature for 1 hr. And then pyridine was added to the reaction vessel and cellulose adduct was recovered by centrifugation (3,000 rpm, 2 min).

iv) Acetylation of unreacted 5'hydroxyl groups

The cellulose adduct obtained as above was suspended in a solution of pyridine-acetic anhydride (10:1 v/v, 5.5 ml) and stirred at room temperature for 30 min. The cellulose-product (113.9 mg) was obtained by repeated centrifugation (3,000 rpm, 2 min) in pyridine (5 ml), washing with methanol (15 ml) and drying in vacuo at room temperature for 30 minutes. The cellulose adduct (DMTrOTpoA$^{Bz}$poTpoG$^{iB}$po$^{Ac}$Upo-Cellulose) can be used for the next coupling step.

(2) Synthesis of DMTrOG$^{iB}$poG$^{iB}$poC$^{Bz}$poTpoA$^{Bz}$poTpoG$^{iB}$-po$^{Ac}$Upo-cellulose DMTrOG$^{iB}$poG$^{iB}$poC$^{Bz}$poTpoA$^{Bz}$poTpoG$^{iB}$-po$^{Ac}$Upo-cellulose was synthesized from DMTrOT-poA$^{Bz}$poTpoGT$^{iB}$po$^{Ac}$Upo-cellulose (113.9 mg) and DMTrOG$^{iB}$poG$^{iB}$ poC$^{Bz}$(43.7 mg) using conditions similar to those set out.

(3) Synthesis of DMTrOA$^{Bz}$poC$^{Bz}$poC$^{Bz}$poG$^{iB}$poG$^{iB}$poC$^{Bz}$poTpoA$^{Bz}$-poTpoG$^{iB}$po$^{Ac}$ Upo-Cellulose DMTrOAT$^{Bz}$poC$^{Bz}$poC$^{Bz}$poG$^{iB}$poG$^{iB}$poC$^{Bz}$poT-poA$^{Bz}$poTpog$^{iB}$po$^{Ac}$Upo-cellulose (105.8 mg) was synthesized from DMTrOG$^{iB}$poG$^{iB}$poC$^{Bz}$poTpoG$^{iB}$-po$^{Ac}$Upo-cellulose (109.5 mg) and DMTrOA$^{Bz}$poC$^{B}$-$_z$poC$^{Bz}$po-CE (44.0 mg) using similar conditions.

(4) Synthesis of DMTrOC$^{Bz}$poC$^{Bz}$poG$^{iB}$poA$^{Bz}$poC$^{Bz}$poC$^{Bz}$poG$^{iB}$po-G$^{iB}$poC$^{Bz}$poTpoA$^{Bz}$poTpoG$^{iB}$po$^{Ac}$Upo-cellulose DMTrOC$^{Bz}$poC$^{Bz}$poG$^{iB}$poA$^{Bz}$poC$^{Bz}$poC$^{Bz}$poG$^{iB}$-poG$^{iB}$poC$^{Bz}$poTpoA$^{Bz}$poTpoG$^{iB}$po$^{Ac}$Upo-cellulose (94.5 mg) was synthesized from DMTrOA$^{Bz}$poC$^{B}$-$_z$poC$^{Bz}$poG$^{iB}$poG$^{iB}$poC$^{Bz}$poTpoA$^{Bz}$poTpoG$^{iB}$-po$^{Ac}$Upo-cellulose (105.8 mg) and DMTrOC$^{Bz}$poC$^{B}$-$_z$poG$^{iB}$po-CE (43.5 mg) using similar conditions.

(5) Synthesis of DMTrOA$^{Bz}$poA$^{Bz}$poA$^{Bz}$poC$^{Bz}$poC$^{Bz}$poG$^{iB}$poA$^{Bz}$-poC$^{Bz}$poC$^{Bz}$poG$^{iB}$poG$^{iB}$poC$^{Bz}$poTpoA$^{Bz}$poTpoG$^{iB}$-po$^{Ac}$Upo-cellulose DMTrOA$^{Bz}$poA$^{Bz}$poA$^{Bz}$poC$^{Bz}$poC$^{Bz}$poG$^{iB}$poA$^{Bz}$-poC$^{Bz}$poC$^{Bz}$poG$^{iB}$poG$^{iB}$poC$^{Bz}$poTpoA$^{Bz}$poTpoG$^{iB}$-po$^{Ac}$Upo-cellulose (90.4 mg) was synthesized from DMTrOC$^{Bz}$poC$^{Bz}$poG$^{iB}$poA$^{Bz}$poC$^{Bz}$poC$^{Bz}$poG$^{iB}$-pog$^{iB}$poC$^{Bz}$poTpoA$^{Bz}$poTpoG$^{iB}$po$^{AC}$Upo-cellulose (94.5 mg) and DMTrOA$^{Bz}$poA$^{Bz}$poA$^{Bz}$po-CE (45.1 mg) using similar conditions. At this final process, it was not necessary to protect the unreacted 5'-hydroxy group with an acetyl group.

(6) Synthesis of HOApAPAPCpCpGpApCpCpGpGPCPTpApT-pGOH:

DMTrOA$^{Bz}$poA$^{Bz}$poA$^{Bz}$poC$^{Bz}$poC$^{Bz}$poG$^{iB}$poA$^{Bz}$-poC$^{Bz}$poC$^{Bz}$poG  $^{iB}$poG$^{iB}$poC$^{Bz}$poTpoA$^{Bz}$poTpoG$^{iB}$-po$^{AC}$Upo-cellulose (90.4 mg) was treated with 0.5 M N,N,N',N'-tetramethylguanidinium pyridine 2-aldoximate (in dioxane-H$_2$O (1:1 v/v, 1 ml)) at 20° C. for 20 hrs in a sealed tube. To the reaction mixture 28% (w/w) aqueous ammonia (12 ml) was added, and the mixture was heated at 60° C. for 2 hrs. The solid cellulose was removed by filtration and washed with water (10 ml). The filtrate and washed solution were evaporated to dryness, and the residue was treated with 80% aqueous acetic acid (25 ml) at room temperature for 15 mins. After removal of the solvents, the residue was dissolved in 0.1 M triethylammonium carbonate buffer (pH 7.5, 25 ml) was washed with diethylether (3 x 25 ml). Aqueous layer was evaporated to dryness and the residue was dissolved in 0.1 M triethylammonium carbonate buffer (pH 7.5, 2 mins) to yield crude HOApApApCpCpG-pApCpCpGpGpCpTpApTpGOH in the solution.

(7) Purification of HOApApApCpCpGpApCpCpGpGpCpTpApT-pGOH i) First purification of the crude product was performed by column chromatography on Biogel P2 (24 x 2.6 cm ID). The fractions corresponding to the first eluted peak (50 mM NH$_4$OAc, 0.1 mM EDTA, 1 ml/min) were collected and freeze-dried to give the first purified product.

ii) Second purification of the first purified product was performed by HPLC on CDR-10 (25 cm x 4.6 mm ID) using a linear gradient of 1M NH4OAc-10% (v/v) aqueous ethanol to 4.5 M NH4OAc-10% (v/v) aqueous ethanol (80 min, 1 ml/min, 60° C) to give the second purified product.

iii) Third purification of the second purified product was performed by reverse phase HPLC (Rp-18-5μ(×77), 15 cm ×4 mm ID) using a linear gradient of 0.1 M NH4OAc to 0.1 M NH4OAc 15% (v/v) aqueous CH3CN (40 min, 1.5 ml/min, room temperature) to give the final purified product (HOApApApCpCpGpApCpCpGpGpCpTpApT-pGOH).

(8) Analysis of oligonucleotide (HOApApApCpCpGpApCpCpGpGpCpTpApT-pGOH)

i) Digestion by phosphodiesterase

The mixture of HOApApApCpCpG-pApCpCpGpGpCpTpApTpGOH (5 μg, 61.7 μl), 0.2 M MgCl2 (10 μl), 0.2 M Tris-HCl (pH 8.5) (10 μl) and 0.1 mM EDTA in an aqueous solution (13.3 μl) was treated with phosphodiesterase (5 unit, 5 μl) at 37° C. for 20 min, and then heated at 100° C. for 2 min.

ii) Analysis by HPLC

The oligonucleotide in the reaction mixture was analyzed by HPLC (CDR-10, 25 cm×4.6 mm ID) using a linear gradient of water to 2.0 M NH4OAc (pH 3.4) (40 min, 1.5 ml/min, 60° C.). From each peak area observed, its nucleotide composition was determined comparing with area of a standard sample.

Calcd: $pC_{OH}$ 5,000, $pA_{OH}$ 4,000, $pT_{OH}$ 2,000, $pG_{OH}$ 4,000 Observed: $pC_{OH}$ 4,767, $pA_{OH}$ 4,127, $pT_{OH}$ 2,054, $pG_{OH}$ 4,052

EXAMPLE 2

Synthesis of oligonucleotides (A1, A2, B1, B2, C1, C2, D1, D2, E1, E2, F1, F2, G2, H1, H2, I1, I2, J1, J2, K1, K2, L1, L2, M1, M2, N1, N2, 01 and 02):

Following oligonucleotides were prepared by a similar manner to that of G1 described in Example 1.

(1) HOApApTpTpCpApTpGpGpGpTOH (A1)
(2) HOTpTpTpCpApGpGpApCpCpCpApTpGOH (A2)
(3) HOCpCpTpGpApApApCpTpCpTpGpTpGOH (B1)
(4) HOCpApGpCpGpCpCpGpCpApCpApGpAp-GOH (B2)
(5) HOCpGpGpCpGpCpTpGpApApCpTpGpG-pTOH (C1)
(6) HOApGpApGpCpGpTpCpApApCpCpApGpT-pTOH (C2)
(7) HOTpGpApCpGpCpTpCpTpGpCpApApTpT-pTOH (D1)
(8) HOCpCpApCpApTpApCpApApApTpTpGpCOH (D2)
(9) HOGpTpApTpGpTpGpGpTpGpApTpCpG-pTOH (E1)
(10) HOTpApGpApApApCpCpApCpGpApTp-CpAOH (E2)
(11) HOGpGpTpTpTpCpTpApCpTpTpCpApAp-COH (F1)
(12) HOGpGpTpCpGpGpTpTpTpGpTpTpGpApAp-GOH (F2)
(13) HOGpCpTpGpGpApGpCpCpApTpApGpC-pCOH (G2)
(14) HOGpCpTpCpCpApGpCpTpCpTpCpGpT-pCOH (H1)
(15) HOCpGpGpTpGpCpGpCpGpApCpGpApG-pAOH (H2)
(16) HOGpCpGpCpApCpCpGpCpApGpApCpT-pGOH (I1)
(17) HOCpTpApCpGpApTpApCpCpApGpTpCpT-pGOH (I2)
(18) HOGpTpApTpCpGpTpApGpApCpGpApApT-pGOH (J1)
(19) HOGpApApApApCpApGpCpApTpTpCpG-pTOH (J2)
(20) HOCpTpGpTpTpTpCpGpTpTpCpTpT-pGOH (K1)
(21) HOGpGpApGpApTpCpGpCpApApGpApAp-COH (K2)
(22) HOCpGpApTpCpTpCpCpGpCpGpTpC-pTOH (L1)
(23) HOTpApCpApTpTpTpCpCpApGpApCpGpG-pCOH (L2)
(24) HOGpGpApApApTpGpTpApCpTpGpTpGpC-pTOH (M1)
(25) HOTpTpCpApGpTpGpGpApGpCpApCpAp-GOH (M2)
(27) HOCpCpApCpTpGpApApGpCpCpApGp-CpAOH (N1)
(28) HOGpCpGpGpApTpTpTpGpCpTpGpG-pCOH (N2)
(29) HOApApApTpCpCpGpCpGpTpGpApTpAp-GOH (O1)
(30) HOGpAPTpCpCpTpApTpCpApCOH (O2)

Example 3

Synthesis of oligonucleotides (a1, a2, a3, a4, a5, a6, b1, b2, b3, b4, b5, b6, c1, c2, c3, c4, c5, c6, d1, d2, d3, d4, d5, d6, e1, e2, e3, e4, e5, 11, 12 and 13):

The following oligonucleotides were prepared using a protocol similar to that used for G1 described in Example 1.

(1) HOApApTpTpCpApTpGpTpGpTpTOH (a1)
(2) HOApCpTpGpCpCpApGpGpApCpCpCpAp-TOH (a2)
(3) HOApTpGpTpApApApApGpApApGpCpAp-GOH (a3)
(4) HOTpGpGpCpApGpTpApApCpApCpApT-pGOH (a4)
(5) HOTpTpTpApCpApTpApTpGpGpGpTpCpCOH (a5)
(6) HOApApGpGpTpTpTpTpCpTpGpCpTpTpC-pTOH (a6)
(7) HOApApApApCpCpTpTpApApGpApApApT-pAOH (b1)
(8) HOCpTpTpTpApApTpGpCpApGpGpTpCpAOH (b2)
(9) HOTpTpCpApGpApTpGpTpApGpGpCpGpG-pAOH (b3)
(10) HOApTpTpApApApGpTpApTpTpTpCpT-pTOH (b4)
(11) HOApTpCpTpGpApApTpGpApCpCpTpG-pCOH (b5)
(12) HOTpTpCpCpApTpTpApTpCpCpGpCpTpAp-COH (b6)
(13) HOTpApApTpGpGpApApCpCpTpCpTpTpT-pCOH (c1)
(14) HOTpTpApGpGpCpApTpTpTpTpGpApAp-GOH (c2)
(15) HOApApTpTpGpGpApApApApGpApGpGpAp-GOH (c3)

(16) HOTpGpCpCpTpApApGpApApApApGpAp-GOH (c4)
(17) HOTpCpCpApApTpTpCpTpTp-CpApApApAOH (c5)
(18) HOCpTpGpTpCpApCpTpCpTpCpCpTpCpT-pTOH (c6)
(19) HOApGpTpGpApCpApGpApApApApApT-pAOH (d1)
(20) HOApTpGpCpApGpApGpCpCpApApApT-pTOH (d2)
(22) HOCpTpCpTpGpCpApTpTpApTpTpTpT-pTOH (d4)
(23) HOApGpGpApGpApCpApApTpTpTpGpGOH (d5)
(24) HOApApApGpCpTpTpGpApApGp-TpApApAOH (d6)
(25) HOCpApApGpCpTpTpTpTp-CpApApApApAOH (e1)
(26) HOCpTpTpTpApApGpGpApTpGpApCp-CpAOH (e2)
(27) HOGpApGpCpApTpCpCpApApApApGpAp-GOH (e3)
(28) HOCpCpTpTpApApApGpTpTpTpTpG-pAOH (e4)
(29) HOGpGpApTpGpCpTpCpTpGpGpTpCpAp-TOH (e5)
(30) HOTpGpTpGpTpApApTpGpApTpApGOH (11)
(31) HOTpApCpApCpApCpTpCpTpTpTpTOH (12)
(32) HOGpApTpCpCpTpApTpCpApTOH (13)

Example 4

Synthesis of oligonucleotides (m1, m2, LA, LB, LC and LD):

The following oligonucleotide (m1 and m2) were prepared used a protocol similar to that of Example 1.
(1) HOApGpCpTpTpGpApApGpTpApApApApC-pApTpGOH (m1)
(2) HOApApTpTpCpApTpGpTpTpTp-TpApCpTpTpCpAOH (m2)
(3) HOApGpCpTpTpGpApApGpTpApTpGpG-pGOH (LA)
(4) HOGpApCpCpCpApTpApCpTpTpCpAOH (LB)
(5) HOApApTpTpCpGpGpCpCpCpGpCpG-pGOH (LC)
(6) HOGpApCpCpCpGpCpGpGpGpCpCpGOH (LD)

Example 5

Synthesis of oligonucleotides (A, B, C, D, E, F, G, H, I, J, K, L, M and N):
The following oligonucleotides were prepared using a protocol similar to that used in Example 1.
(1) HOApApTpTpTpGpCpCpGpApCpAOH (A)
(2) HOCpGpTpTpApTpGpApTpGpTpCpGpGp-CpAOH (B)
(3) HOTpCpApTpApApCpGpGpTpTpCpTpGpG-pCOH (C)
(4) HOGpApApTpApTpTpTpTpGpCpCpApGpApAp-COH (D)
(5) HOApApApTpApTpTpCpTpGpApApApTpG-pAOH (E)
(6) HOTpCpApApCpApGpCpCpTpCpApTpTp-CpAOH (F)
(7) HOGpCpTpGpTpTpGpApCpApApTpTpApAp-TOH (G)
(8) HOGpTpTpCpGpApTpGpApTpTpApApTpT-pGOH (H)
(9) HOCpApTpCpGpApApCpTpApGpTpTpApAp-COH (I)
(10) HOGpCpGpTpApCpTpApGpTpTpApApCp-TpAOH (J)
(11) HOTpApGpTpApCpGpCpApApGpTpTpCpAp-COH (K)
(12) HOCpTpTpTpTpApCpGpTpGpApApCpT-pTOH (L)
(13) HOGpTpApApApApApGpGpGpTpApTpC-pGOH (M)
(14) HOApApTpTpCpGpApTpApCpCpOH (N)

Example 6

Synthesis of oligonucleotides (SA, AB, SC, SD, SE, SF, SG, and SH):
(1) HOApApTpTpCpApTpGpGpCpTOH (SA)
(2) HOGpGpTpTpGpTpApApGpApApCpTpTpC-pTOH (SB)
(3) HOTpTpTpGpGpApApGpApCpTpTpTOH (SC)
(4) HOCpApCpTpTpCpGpTpGpTpTpGpApTpAp-GOH (SD)
(5) HOTpTpApCpApApCpApCpApGpCpCpApTpGOH (SE)
(6) HOCpCpApApApApApGpApApApGpTpTpCOH (SF)
(7) HOCpGpApApGpTpGpApApApGpTpCpT-pTOH (SG)
(8) HOGpApTpCpCpTpApTpCpApApCpAOH (SH)

EXAMPLE 7

Preparation of IGF-I gene

Aliquots of each oligonucleotides (A1-O1) (0.4 nM) were phosphorylated with 4 units of T4 polynucleotide kinase (made by BRL) in 100 μl of a solution containing 74 mM Tris-HCl (pH 7.6), 10 mM DTT, 1.6 mM mercaptoethanol, 10 mM MgCl$_2$ and 0.5 mM ATP for 20 minutes at 37° C. After the reaction was completed, the enzyme in the reaction mixture was deactivated by incubation at 100° C. for 5 minutes. Ligation of the phosphorylated oligonucleotides was carried out as shown in FIG. 3 to μfirst give fragment ten blocks fragment and ultimately the IGF-I gene for cloning. Ligations were carried out with T4 DNA ligase (7 units) in a solution containing 100 mM ATP (0.5 μl) for 23 hours at 4° C. (standard conditions). The ligation products of oligonucleotides in each step were identified by staining with ethidium bromide following electroelution on a 2–16% gradient PAGE in tris-EDTA buffer.

EXAMPLE 8

Molecular cloning of the IGF-I gene

Plasmid pBR322 was digested with BamHI and EcoRI restriction endonucleases. Reaction was terminated by heating at 65° C. for 5 minutes and the fragments separated by electrophoresis on a 0.5% agarose gel. The 3985 bp large fragment from pBR322 was recovered and ligated with T4 DNA ligase for 18 hours at 12° C. to the 224bp IGF-I gene. The ligated mixture was transformed into E. coli HB101 by Kushner's method and ampicillin resistant transformants were selected on the plate containing tetracycline (25 μg/ml). Plasmid DNA isolated from one of five clones resistant to ampicillin and sensitive to tetracycline was digested with EcoRI and BamHI and compared with appropriate size markers. The expected 224 bp IGF-I fragment was generated. This plasmid which was characterized by complete nucleotide sequencing of the IGF-I gene was named pSdMl and was used for the construction of expression vector.

EXAMPLE 9

Construction of the synthetic tryptophan promoter gene I

Each oligonucleotides (B-M) of block I, II, III were phosphorylated with T4 polynucleotide kinase and then ligated with T4 DNA ligase as described above. These blocks (I-III) and unphosphorylated oligonucleotides (A, N) were condensed successively. The last ligation product was purified by preparative 7.5% PAGE to give the 107 bp synthetic trp promoter I gene.

EXAMPLE 10

Molecular cloning of the synthetic trp promoter I gene

Plasmid pBR325 was digested with EcoRI and then linear pBR325 was ligated with the synthetic trp promoter I gene prepared above. The transformants of *E. coli* HB101 by the above ligation mixture were screened on the plates contained antibiotics to give four $^R$Amp $^S$Cm colonies. The plasmids obtained from four colonies were digested with HpaI, respectively. The fragments obtained from these plasmids by HindIII and EcoRI digestion were compared with the fragments of pBR325 by HindIII and EcoRI digestion. One of four plasmids has the correct directed promoter gene (synthetic trp promoter I gene) and the other were inserted in reverse direction.

EXAMPLE 11

Construction and cloning of the synthetic trp promoter II gene

Trp promoter II gene was constructed by the method as described above. The synthetic gene was ligated with EcoRI, BamHI fragment of pBR322 and then *E. coli* HB101 was transformed with the ligation product. The plasmid obtained from the transformant of $^R$Amp and $^S$Tet was digested with HpaI to confirm a band (4.1 kbp), and then digested with BamHI to confirm a band of 90 bp on PAGE. Moreover, the fragment of 56 bp by EcoRI-BamHI digestion was confirmed by the comparison with size marker on PAGE. This plasmid was named pTrpEB7 and used in the construction of expression vector.

EXAMPLE 12

Construction of IGF-I expression vector (pSdMl-322trp)

Trp promoter II vector (pAtrpEB7) was digested with EcoRI and BamHI to give a large fragment (4.1 kbp) by PAGE. This fragment was ligated with the IGF-I gene prepared from a plasmid pSdMl. The ligated mixture was transformed into *E. coli* HB101 and ampicillin resistant and tetracycline-sensitive transformants were selected. The plasmid obtained pSdMl-322trp, was digested with EcoRI and BamHI to confirm the IGF-I gene (224bp) on 7.5% PAGE.

EXAMPLE 13

Sequencing of the IGF-I gene and of the synthetic trp promoter I gene

For the sequencing of the IGF-I gene and the synthetic trp promoter I gene by the Maxam-Gilbert method, plasmid pSdMl-322trp was digested with EcoRI and treated with bacteria alkaline phosphatase at 37° C. for 1 hour. After phenol extraction and ethanol precipitation the plasmid was phosphorylated with T4 polynucleotide kinase in the presence of γ-32P-ATP at 37° C. for 1 hour, finally was digested with HinfI to afford two fragments (1100 bp, 480 bp) Each fragment was sequenced according to the manual of Maxam-Gilbert method [A. Maxam and W Gilbert, Proc. Natl. Acad. Sci. USA 74, 560(1977)]. The resulting sequence of IGF-I and synthetic trp promoter I gene agreed with that designed.

EXAMPLE 14

Expression of the IGF-I gene:

An overnight culture of *E. coli* F-3 (which is *E. coli* HB101 containing plasmid pSdMl-322trp) in L broth containing 20 μg/ml ampicilline was diluted 1 : 25 in M9 medium containing 0.2% glucose, 0.5% casamino acid (acid-hydrolyzed casein) and 50 μg/ml vitamin B1. β-indole acrylic acid was added to a final concentration of 10 μg/ml when A was 0.4. Then the cells were incubated for 3 hours and collected by centrifugation (6 krpm, 4° C., 5 minutes). Cell were opened by sonication and cleared of debris by centrifugation. The supernatants were mixed with 3M acetic acid. The precipitate was removed by centrifugation (20 krpm, 4° C., 10 minutes), the supernatants were freeze-dried. For assay the sample was suspended in 4 ml of medium (0.01 M PBS, 0.025M EDTA, and 0.5% BSA) and adjusted at pH 7-8 with 0.1 N NaOH. After removal of insoluble substance by centrifugation, the supernatants were stored at −20° C. until assay.

EXAMPLE 15

RIA of IGF-I

The RIA of IGF-I was followed the method established by N. Yanaihara. With 0.1 ml of the above sample or standard sample (IGF-I fragment (26–46)) sample buffer [0.5% BSA in 0.01M PBS, 0.025 M EDTA (pH 7.4) (0.4 ml)], rabbit antiserum (0.1 ml) of IGF-I (26–46) and $^{125}$I-IGF-I (26–46) (0.1 ml) were mixed. The mixture was allowed to stand for 48 hours at 4° C., and then added with rabbit serum (0.1 ml), rabbit Y-globulin antiserum (0.1 ml) and 5% PEG6000 (0.9 ml). After standing for additional 2 hours at 4° C. the pellet was collected by centrifugation (3 krpm, 4° C., 30 minutes). Radioactivity was measured by γ-counter. The content of IGF-I was calculated from this radioactivity.

EXAMPLE 16

Sequencing of the IGF-I gene in plasmid pSdMl

For sequencing the IGF-I gene, plasmid pSdMl was digested with EcoRI and then treated with AMV reverse transcriptase (purchased from Seikagaku Kogyo Co., Ltd.) in the presence of α-32P-ATP at 37° C. for 30 minutes. The linear plasmid labeled with $^{32}$P was digested with BamHI to give two fragments (224 bp, 4.0 kbp). The smaller fragment (224 bp) was recovered by preparative polyacrylamide gel electrophoresis and sequenced according to the Maxam-Gilbert method. On the other hand, plasmid pSdMl was digested with BamHI firstly and then labeled with $^{32}$P as described above. The linear plasmid was digested with EcoRI to give two fragments (226 bp, 4.0 kbp). The smaller fragments (224 bp) was analyzed the Maxam-Gilbert method as above. The results of sequencing from both side of the IGF-I gene were agreed with the designed IGF-I gene.

EXAMPLE 17

Preparation of the protein peptide LH gene

Aliquots of each oligonucleotides (a2-12) (0.4 nM) were phosphorylated with 2.5 units of T4 polynucleotide kinase in 40 μl of a solution containing 50 mM Tris-HCl (pH 7.6), 20 mM DTT, 50 μg/ml BSA, 1 mM spermidine, 10 mM MgCl₂ and 2 mM ATP for 3 hours at 37° C. After the reaction was completed, the enzyme in the reaction mixture was deactivated by incubation at 100° C. for 5 minutes. Ligation of the phosphorylated oligonucleotides and two oligonucleotides (a1 and 13) was carried out as shown in FIG. 7 to first give six block fragments and ultimately protein/peptide LH gene (236 bp) for cloning. Ligation was carried out with T4 DNA ligase (5 units) in a solution containing 50 mM ATP (1 μl) for 5 hours at 16° C. The ligation products of oligonucleotides in each step were identified by staining with ethidium bromide following electroelution on a 2–16% gradient PAGE in Tris-EDTA buffer.

EXAMPLE 18

Molecular cloning of protein/peptide LH gene

A protein/peptide LH gene (236 bp), which synthesized as set out above, was inserted into pBR 322 using a similar method to that of Example 8. The plasmid (pLH107) obtained from E. coli HB101 transformant was characterized by restriction enzyme analysis to have protein/peptide LH (236bp).

EXAMPLE 19

Construction of synthetic trp promoter II gene

Each oligonucleotides (B to SG) of block I', II', III' and IV' were phosphorylated with T4 polynucleotide kinase and then ligated with T4 DNA ligase as described above. These blocks (I' to IV') and unphosphorylated oligonucleotides (A and SH) were condensed successively. The last ligation product was purified by preparative 7.5% PAGE to give the 163 bp synthetic trp promoter II gene.

EXAMPLE 20

Cloning of the synthetic trp promoter II gene

The trp promoter II gene constructed in Example 19 was ligated with EcoRI, BamHI fragment of pBR322 and then E. coli HB101 was transformed with the ligation product. The plasmid obtained from the transformant of $^R$Amp and $^S$Tet was digested with HpaI to confirm a band (4.1 kbp), and then digested with BamHI to confirm a band of 90 bp on PAGE. Moreover, the fragment of 56 bp by EcoRI-BamHI digestion was confirmed by the comparison with a size marker on PAGE. This plasmid was named pTrpEB7 and used for the construction of an expression vector.

EXAMPLE 21

Construction of protein/peptide LH expression vector (pLHtrp)

The trp promoter II vector (pTrpEB7) prepared in Example 20 was digested with EcoRI and BamHI to give a large fragment (4.1 kbp) by preparative agarose gel electrophoresis. This fragment was ligated with protein peptide LH gene prepared from a plasmid pLH107 by EcoRI and BamHI digestion. The ligated mixture was transformed into E. coli HB101 to give ampicillin resistant and tetracycline sensitive transformants. The plasmid (pLHtrp) obtained from the transformant was digested with EcoRI and BamHI to confirm protein peptide LH gene (236 bp) on 7.5% PAGE.

EXAMPLE 22

Construction of IGF-I expression vector pLHSdMmtrp

Plasmid pSdMl was digested with EcoRI and BamHI to give IGF-I gene (224 bp). On the other hand, oligonucleotide (m2) prepared in Example 4 (2) was phosphorylated with T4 polynucleotide kinase as described in Example 7. The phosphorylated oligonucleotide, oligonucleotide ml prepared in Example 4 (1) and IGF-I gene (224 bp) were mixed and treated with T4 ligase in a solution containing 100mM ATP for 20 hours at 4° C. The ligation mixture was digested with BamHI and then purified by preparative PAGE to give IGF-I gene with linker (242 bp). The gene (242 bp) was ligated with the fragment obtained from pLHtrp by HindIII-BamHI digestion, and then the ligation mixture was transformed into E. coli HB101. The E. coli HB101 containing plasmid pLHSdMmtrp was named E. coli F-6 and deposited with Fermentation Research Institute Agency of Industrial Science and Technology (1-3, Higashi 1 chome Yatabe-machi Tsukuba-gun Ibaraki-ken 305, Japan) under deposit number of FERM P-7848 on Sept. 17, 1984, and then converted to Budapest Treaty deposit with of the same depository on February 28, 1985 under the new deposit number of FERM BP-729. The plasmid (pLHSdMmtrp) obtained from the transformant was digested with EcoRI and BamHI (198, 224 bp), HindIII and BamHI (242 bp), HpaI-BamHI (456 bp) to confirm the synthetic trp promoter I, protein peptide LH and IGF-I gene on 7.5% PAGE.

EXAMPLE 23

Expression of a gene coding for IGF-I fused with protein peptide LH (Type I) in E. coli F-6:

An overnight culture of E. coli F-6 (which is E. coli HB101 containing plasmid pLHSdMmtrp) (FERM P-7848) in L broth containing 50μg/ml ampicillin was diluted 1:20 in M9 medium containing 0.2% glucose, 0.5% casamino acid (acid-hydrolyzed casein), 50 μg/ml vitamin B1 and 25 μg/ml ampicillin. β-Indole acrylic acid was added to a final concentration of 10μg/ml when A600 was 0.5. Then the cells were incubated for 2 hours and collected by centrifugation (5 krpm, 4° C., 5 minutes).

EXAMPLE 24

Isolation and purification of IGF-I (1) Isolation and purification of fused IGF-I (Type I)

Wet cell paste (60 g) was suspended in 150 ml of 10 mM PBS-EDTA (pH 8.0) and cells were lysed by sonication. The cells debris was pelleted by centrifugation at 18,000 rpm for 30 minutes. The pellet was dissolved in 50 ml of 0.1 M Tris-HCl (pH 8.0)/8 M urea and 0.1 M dithiothreitol and centrifuged at 35,000 rpm for 30 minutes at 25° C. The supernatant was collected and applied to a Sephacryl S300 superfine column (5.0×86.6 cm; 1700 ml resin) equilibrated with 0.1 M Tris-HCl (pH 8.0)/8 M urea and 10 mM 2-mercaptoethanol. Elution was carried out at 4° C. with equilibration buffer, at a flow rate of 0.6 ml/min. Sephacryl S 300 chromatography was conducted and fractions of 17 ml were collected. Sephacryl S300 chromatography was conducted. Assays were performed immediately following fractionation for all chromatography steps. Active fraction were collected and the pooled fraction of 255 ml was dialyzed for 3 hours at room temperature against 8 liters of 1 M acetic acid aqueous solution and then overnight against 8 liters of fresh 1 M acetic acid aqueous solution. The fraction dialyzed was lyophilized to give fused IGF-I (Type I) of 450 mg which contains a desired component. The fused IGF-I (Type I) shows a band at the position of molecular weight 15,500 on 15% SDS PAGE.

(2) Elimination of protein/peptide LH (Type I) from fused IGF-I (Type I) with cyanogen bromide The fused IGF-I (Type I) (225 mg) obtained by procedure (1) was dissolved in 36 ml of 60% formic acid. Cyanogen bromide (36 mg) was added and the mixture was allowed to react for 3 hours below 25° C. with stirring. After addition of 234 ml of distilled water, formic acid and cyanogen bromide were removed by lyophylization. The residue was dissolved in 36 ml of 1M Tris-HCl (pH 8.0)/8 M urea and 50 mM 2-mercaptoethanol. The resulting solution was dialyzed twice for 3 hours at room temperature against 400 ml of 0.01 M AcONH$_4$ (pH 4.6)/8 M urea and 50 mM 2-mercaptoethanol (Buffer A) and then overnight against 400 ml of fresh Buffer A. The solution dialyzed was applied to a cationic ion exchange resin CM 52 column (1.6 x 7.5 cm; 15 ml resin) equilibrated with Buffer A. The column was washed with Buffer A (60 ml) at room temperature at a flow rate of 0.25 ml/min and eluted with a linear gradient from Buffer A (120 ml) to 0.2 M AcONH$_4$/8 M urea and 50 mM 2-mercaptoethanol (120 ml). Fractions (from No. 57 to No. 100) of 2.9 ml were collected.

(3) High performance liquid chromatography

The pooled fraction obtained by procedure (2) was applied onto HPLC using the following conditions:
column: Beckman Ultrapore RPSC (4.6×75 mm)
flow rate: 1 ml/min
elution: linear gradient from 10% to 60 %
acetonitrile in 0.01 M trifluoroacetic
acid over 50 minutes.

The chromatography was repeated 15 times and fractions containing reduced IGF-I were collected. The main peak with a retention time of 29.32 minutes corresponds to reduced IGF-I. The thus reduced IGF-I was obtained about 2.4 mg by the procedures described above. The reduced IGF-I was converted to oxidize IGF-I by usual manner of refolding. The IGF-I was superimposed with authentic IGF-I gifted by Dr. Humbel on HPLC.

(4) Amino acid analysis and sequence analysis of IGF-I

The amino acid composition of IGF-I was determined using a Walters amino acid analysis system. The amino acid sequence of IGF-I was determined using a combination of Edman's method (DIBITC method) [J. Y. Chang et al: Biochem. J., 153, 607(1976), Biochim. Biophys. Acta., 78, 188(1979)]and the carboxypeptidase method as shown in FIG. 19.

EXAMPLE 25

Construction of IGF-I expression vector pLHSdMwtrp

Plasmid pSdM1 was digested with EcoRI and BamHI to give the IGF-I gene (224 bp), which was digested with AvaII. The larger fragment (215 bp) was recovered by preparative PAGE. On the other hand, oligonucleotide (LB) prepared in Example 4 (4) was phosphorylated with T4 polynucleotide kinase as described in Example 7. The phosphorylated oligonucleotide, oligonucleotide LA prepared in Example 4 (3) and the IGF-I fragment (215 bp) prepared as above were mixed and treated with T4 ligase in a solution containing 100 mM ATP for 20 hours at 4° C. The ligation mixture was digested with BamHI and then purified by preparative PAGE to give IGF-I gene (230 bp) with linker. The IGF-I gene (230 bp) was ligated with the fragment obtained from PLHtrp by HindIII and BamHI digestion, and then the ligation mixture was transformed into *E. coli* HB 101. The plasmid (pLHSdMwtrp) obtained from the transformant was digested with EcoRI and BamHI (416 bp), EcoRI and PstI (859 bp), HindIII and BamHI (230 bp) to confirm this plasmid gene on 7.5% PAGE. The *E. coli* HB101 containing plasmid pLHSdMwtrp was named *E. coli* F-7.

EXAMPLE 26

Expression of a gene coding for IGF-I fused with protein peptide LH (Type II) in *E. coli* F-7:

An overnight culture of *E. coli* F-7 (which is *E. coli* HB101 containing plasmid pLHSdMwtrp) in L broth containing 50 μg/ml ampicillin was diluted 1:20 in M9 medium containing 0.2% glucose, 0.5% casamino acid (acid-hydrolyzed casein), 50 μg/ml vitamin B1 and 25 μg/ml ampicillin. 8-Indole acrylic acid was added to a final concentration of 10 μg/ml when A600 was 0.5. Then the cells were incubated for 2 hours and collected by centrifugation (5 krpm, 4° C., 5 minutes).

EXAMPLE 27

Isolation and purification of IGF-I (1) Isolation and purification of IGF-I fused with protein/peptide LH (Type II)

Wet cell paste (60 g) was suspended in 150 ml of 10 mM PBS-EDTA (pH 8.0) and cells were lysed by sonication. The cell debris was pelleted by centrifugation at 18,000 rpm for 30 minutes. The pellet was dissolved in 50 ml of 0.1 M Tris HCl (pH 8.0)/8 M urea and 0.1 M dithiothreitol and centrifuged at 40,000 rpm for 30 minutes at 20° C. The supernatant was collected and applied to a Sephacryl S 300 superfine column (5.0×86.6 cm; 1,700 ml resin) equilibrated with 0.1 M Tris HCl (pH 8.0)/8 M urea and 10 mM 2-mercaptoethanol. Elution was carried out at 4° C. with equilibration buffer at a flow rate of 0.6 ml/ml. Sephacryl S 300 chromatography was conducted and fractions of 17 ml were collected. Assays were perform immediately following fractionation for all chromatography steps. Active fraction were collected and the pooled fractions of 204 ml were dialyzed for 3 hours at room temperature against 8 liters of 1 M acetic acid aqueous solution and then overnight against 8 liters of fresh 1 M acetic acid aqueous solution. The fraction dialyzed was lyophilized to give fused IGF-I (Type II) of 450 mg which contains a desired component. The crude fused IGF-I (Type II) was purified by reverse phase HPLC (ultrapore RPSC column) using a linear gradient of 10% CH$_3$CN (0.01 M TFA) to 60% CH$_3$CN (0.01 M TFA) to give the purified fused IGF-I (Type II).

(2) Cleavage of protein/peptide LH (Type II) from the fused IGF-I (Type II)

(a) Cleavage of protein/peptide LH (Type II) from fused IGF-I (Type II) with BNPS-skatole The fused IGF-I (Type II) (830 μg) was treated with BNPS-skatole (297 μg) in 70% acetic acid at 0° C. for 3 hours To the reaction mixture 2-mercaptoethanol (120 μl) was added, and then the solvent was evaporated in vacuo. The residue was dissolved in 6 M guanidine, 50 mM Tris HCl buffer (2 ml) and washed CHCl$_3$ (2 ml). The aqueous then purified by reverse phase HPLC (RPSC column) to give a IGF-I sulfoxide (50 μg).

(b) Cleavage of protein/peptide LH (Type II) from fused IGF-I (Type II) with NCS in urea The fused IGF-I (Type II) (71 μg) was treated with NCS (6.6 μg) in a mixture of acetic acid (1 ml), urea (1 g) and water (2 ml) at 0° C. for 24 hours. The reaction mixture was neutralized with Tris, treated with 2-mercaptoethanol (20 ml), and then purified by reverse phase HPLC (RPSC column) to give IGF-I sulfoxide (4.2

(3) Reduction of IGF-I sulfoxide with thioglycolic acid

IGF-I sulfoxide (17 μg) in a solution (400 ml) of 5 M thioglycolic acid and 6 M urea was allowed at 50° C. for 3.5 hours. After addition of 6M guanidine (1 ml) and 2-mercaptoethanol (100 μl), the mixture was adjusted pH 8.0 with Tris, and then purified by reverse phase HPLC (RPSC column) to give a pure reduced IGF-I (7 μg).

EXAMPLE 28

Construction of IGF-I expression vector pLHSdMctrp

The plasmid pSdMl was digested with AvaII to give the gene (640 bp) containing IGF-I gene, which was digested with BamHI and the larger fragment (215 bp) was recovered by preparative PAGE. On the other hand, oligonucleotides (LC and LD) prepared in Examples 4(5) and 4(6), were phosphorylated with T4 polynucleotide kinase as described in Example 7. The phosphorylated oligonucleotides and the IGF-I fragment (215 bp) prepared as above were mixed and treated with T4 DNA ligase in a solution containing 100 mM ATP for 24 hours at 4° C. The ligation mixture was digested with EcoRI and BamHI, and then purified by preparative PAGE to give IGF-I gene (230 bp) with linker. The IGF-I gene (230 bp) was ligated with the fragment (4 kbp) obtained from pBR322 by EcoRI and BamHI digestion, and then the ligation mixture was transformed into E. coli DH1. The plasmid pSdMc obtained from the transformant was digested with EcoRI and BamHI (230 bp) to confirm this plasmid gene on 7.5% PAGE. The plasmid pSdMc was digested with EcoRI and BamHI, the smaller fragment (230 bp) was recovered by preparative PAGE. On the other hand, oligonucleotide (m2) prepared in Example 4 (2) was phosphorylated with T4 polynucleotide kinase as described in Example 7. The phosphorylated oligonucleotide, oligonucleotide ml prepared in Example 4 (1) and IGF-I gene (230 bp) were mixed and treated with T4 ligase in a solution containing 100mM ATP for 20 hours at 4° C. The ligation mixture was digested with BamHI and then purified by preparative PAGE to give IGF-I gene with linker (242 bp). The gene (248 bp) was ligated with the fragment obtained from pLHtrp by HindIII-BamHI digestion, and then the ligation mixture was transformed into E. coli HB101. The E. coli HB101 containing plasmid pLHSdMctrp was named E. coli F-8. The plasmid (pLHSdMctrp) obtained from the transformant was digested with EcoRI and BamHI (198, 230 bp), HindIII and BamHI (248 bp), HpaI-BamHI (456 bp) to confirm the synthetic trp promoter I, protein/peptide LH and the IGF-I gene on 7.5% PAGE.

EXAMPLE 29

Expression of a gene coding for IGF-I fused with protein/peptide LH (Type III):

An overnight culture of E. coli F-8 (which is E. coli HB101 containing plasmid pLHpSdMctrp) in L broth containing 50μg/ml ampicillin was diluted 1:20 in M9 medium containing 0.2% glucose, 0.5% casamino acid (acid-hydrolyzed casein), 50 μg/ml vitamin B1 and 25 μg/ml ampicillin. 8-Indole acrylic acid was added to a final concentration of i0μg/ml when A600 was 0.5. Then the cells were incubated for 2 hours and collected by centrifugation (5 krpm, 4° C., 5 minutes).

EXAMPLE 30

Isolation and purification of IGF-I (1) Isolation and purification of IGF-I fused with protein/peptide LH (Type III)

Wet cell paste (60 g) was suspended in 150 ml of 10 mM PBS-EDTA (pH 8.0) and cells were lysed by sonication. The cell debris was pelleted by centrifugation at 18,000 rpm for 30 minutes. The pellet was dissolved in 50 ml of 0.1 M Tris HCl (pH 8.0)/8 M urea and 0.1 M dithiothreitol and centrifuged at 40,000 rpm for 30 minutes at 20° C. The supernatant was collected and applied to a Sephacryl S 300 superfine column (5.0 x 86.6 cm; 1,700 ml resin) equilibrated with 0.1 M Tris HCl (pH 8.0)/8 M urea and 10 mM 2-mercaptoethanol. Elution was carried out at 4° C. with equilibration buffer at a flow rate of 0.6 ml/ml. Sephacryl S 300 chromatography was conducted and fractions of 17 ml were collected. Assays were perform immediately following fractionation for all chromatography steps. Active fraction were collected and the pooled fraction of 204 ml were dialyzed for 3 hours at room temperature against 8 liters of a 1 M acetic acid aqueous solution and then overnight against 8 liters of fresh 1 M acetic acid aqueous solution. The fraction dialyzed was lyophilized to give fused IGF-I (Type III) of (450 mg.) which contained the desired component. The crude fused IGF-I (Type III) was purified by reverse phase HPLC (ultrapore RPSC column) using a linear gradient of 10% CH CN (0.01 M TFA) to 60% CH$_3$CN (0.01 M TFA) to give a purified fused IGF-I (Type III).

(2) Cleavage of protein//peptide LH (Type III) from the fused IGF-I (Type III) with collagenase The solution of the fused IGF-I (Type III) (25 μg) in 8 M urea or 8 M guanidine HCl was diluted with water until 2.4 M (urea) or 2 M (Guanidine HCl). To the solution 500 mM Tris-HCl, 100 mM CaCl$_2$ and 200 mM acetic acid were added and the solution was adjusted at pH 7.2 with 1N HCl, and then 0.1 mM diisopropyl fluorophosphate and collagenase (10 mg) were added. The mixture was gently stirred at 30° C. for 18 hours. The reaction was stopped by addition of guanidine HCl until final concentration of 8M. After addition of DTT (100 mM/ml), the mixture was analyzed by HPLC. (Column: Beckman Ultrapor RPSC; Flow rate: 1 ml/min; Elution: linear gradient from 10% to 60% acetonitrile in 0.01 M TFA over 50 minutes) to detect a peak corresponding to reduced IGF-I.

What we claim is:

1. A gene encoding IGF-I fused to a protective protein or peptide, in which said protective protein or peptide is a protein or a peptide having a methionine residue as its carboxy-terminal amino acid, is fused to IGF-I through said methionine residue, and is used for the protection of IGF-I from degradation by protease in cells of *E. coli*.

2. The gene of claim 1, which codes for the following amino acid sequence:

```
1                                              10
Cys—Tyr—Cys—Gln—Asp—Pro—Tyr—Val—Lys—Glu—Ala—Glu—Asn—Leu—
                         20
Lys—Lys—Tyr—Phe—Asn—Ala—Gly—His—Ser—Asp—Val—Ala—Asp—Asn—
         30                              40
Gly—Thr—Leu—Phe—Leu—Gly—Ile—Leu—Lys—Asn—Trp—Lys—Glu—Glu—
                              50
Ser—Asp—Arg—Lys—Ile—Met—Gln—Ser—Gln—Ile—Val—Ser—Phe—Tyr—
                    60                                  70
Phe—Lys—Leu—Glu—Val—Lys—His—Glu—Phe—Met—Gly—Pro—Glu—Thr—
                                   80
Leu—Cys—Gly—Ala—Glu—Leu—Val—Asp—Ala—Leu—Gln—Phe—Val—Cys—
                         90
Gly—Asp—Arg—Gly—Phe—Tyr—Phe—Asn—Lys—Pro—Thr—Gly—Tyr—Gly—
  100                                            110
Ser—Ser—Ser—Arg—Arg—Ala—Pro—Gln—Thr—Gly—Ile—Val—Asp—Glu—
                              120
Cys—Cys—Phe—Arg—Ser—Cys—Asp—Leu—Arg—Arg—Leu—Glu—Met—Tyr—
         130
Cys—Ala—Pro—Leu—Lys—Pro—Ala—Lys—Ser—Ala.
```

3. An expression plasmid containing a promoter and the gene as defined in claim 1.

4. *E. coli* containing the expression plasmid as defined in claim 3.

5. An expression plasmid containing a promoter and the gene as defined in claim 1.

6. *E. coli* containing the expression plasmid as defined in claim 5.

7. IGF-I fused to a protective protein or peptide, in which said protective protein or peptide is a protein or a peptide having a methionine residue as its carboxy-terminal amino acid and is fused to IGF-I through said methionine residue, and is used for the protection of IGF-I from degradation by protease in cells of *E. coli*.

8. The IGF-I fused to a protective protein or peptide of claim 7, comprising the following amino acid sequence:

```
1                                              10
Cys—Tyr—Cys—Gln—Asp—Pro—Tyr—Val—Lys—Glu—Ala—Glu—Asn—Leu—
                         20
Lys—Lys—Tyr—Phe—Asn—Ala—Gly—His—Ser—Asp—Val—Ala—Asp—Asn—
         30                              40
Gly—Thr—Leu—Phe—Leu—Gly—Ile—Leu—Lys—Asn—Trp—Lys—Glu—Glu—
                              50
Ser—Asp—Arg—Lys—Ile—Met—Gln—Ser—Gln—Ile—Val—Ser—Phe—Tyr—
                    60                                  70
Phe—Lys—Leu—Glu—Val—Lys—His—Glu—Phe—Met—Gly—Pro—Glu—Thr—
                                   80
Leu—Cys—Gly—Ala—Glu—Leu—Val—Asp—Ala—Leu—Gln—Phe—Val—Cys—
                         90
Gly—Asp—Arg—Gly—Phe—Tyr—Phe—Asn—Lys—Pro—Thr—Gly—Tyr—Gly—
  100                                            110
Ser—Ser—Ser—Arg—Arg—Ala—Pro—Gln—Thr—Gly—Ile—Val—Asp—Glu—
                              120
Cys—Cys—Phe—Arg—Ser—Cys—Asp—Leu—Arg—Arg—Leu—Glu—Met—Tyr—
         130
Cys—Ala—Pro—Leu—Lys—Pro—Ala—Lys—Ser—Ala.
```

9. A process for the production of IGF-I which comprises subjecting IGF-I fused to a protective protein or peptide to a cleavage reaction, in which said protective protein or peptide is a protein or a peptide having a methionine residue as its carboxy-terminal amino acid and is fused to IGF-I through said methionine residue, and (ii) said cleavage reaction is conducted with cyanogen bromide.

10. A process for the production of IGF-I fused to a protective protein or peptide which comprises:
(a) culturing *E. coli* containing an expression plasmid containing a promoter and a gene encoding IGF-I fused to a protective protein or peptide, in which said protective protein or peptide is a protein or a peptide having a methionine residue as its carboxy-terminal amino acid, is fused to IGF-I through said methionine residue, and is used for the protection of IGF-I from degradation by protease in cells of *E. coli*, and
(b) recovering IGF-I fused to said protective protein or peptide from the culture.

11. A process for the production of IGF-I fused to a protective protein or peptide which comprises:
(a) culturing *E. coli* containing an expression plasmid containing a promoter and a gene which encodes the following amino acid sequence:

```
 1                                                      10
Cys—Tyr—Cys—Gln—Asp—Pro—Tyr—Val—Lys—Glu—Ala—Glu—Asn—Leu—
                        20
Lys—Lys—Tyr—Phe—Asn—Ala—Gly—His—Ser—Asp—Val—Ala—Asp—Asn—
 30                                  40
Gly—Thr—Leu—Phe—Leu—Gly—Ile—Leu—Lys—Asn—Trp—Lys—Glu—Glu—
                              50
Ser—Asp—Arg—Lys—Ile—Met—Gln—Ser—Gln—Ile—Val—Ser—Phe—Tyr—
             60                                        70
Phe—Lys—Leu—Glu—Val—Lys—His—Glu—Phe—Met—Gly—Pro—Glu—Thr—
                                    80
Leu—Cys—Gly—Ala—Glu—Leu—Val—Asp—Ala—Leu—Gln—Phe—Val—Cys—
                         90
Gly—Asp—Arg—Gly—Phe—Tyr—Phe—Asn—Lys—Pro—Thr—Gly—Tyr—Gly—
100                                 110
Ser—Ser—Ser—Arg—Arg—Ala—Pro—Gln—Thr—Gly—Ile—Val—Asp—Glu—
                              120
Cys—Cys—Phe—Arg—Ser—Cys—Asp—Leu—Arg—Arg—Leu—Glu—Met—Tyr—
             130
Cys—Ala—Pro—Leu—Lys—Pro—Ala—Lys—Ser—Ala; and
```

(b) recovering IGF-I fused to said protective protein or peptide from the culture.

* * * * *